(12) United States Patent
Kimba

(10) Patent No.: US 8,045,142 B2
(45) Date of Patent: Oct. 25, 2011

(54) POLISHING END POINT DETECTION METHOD, POLISHING END POINT DETECTION APPARATUS AND POLISHING APPARATUS

(75) Inventor: Toshifumi Kimba, Tokyo (JP)

(73) Assignee: Ebara Corporation, Tokyo (JP)

( * ) Notice: Subject to any disclaimer, the term of this patent is extended or adjusted under 35 U.S.C. 154(b) by 446 days.

(21) Appl. No.: 12/314,839

(22) Filed: Dec. 17, 2008

(65) Prior Publication Data

US 2009/0153859 A1    Jun. 18, 2009

(30) Foreign Application Priority Data

Dec. 18, 2007 (JP) .................... 2007-325730
Feb. 19, 2008 (JP) .................... 2008-37442

(51) Int. Cl.
G01J 3/50 (2006.01)
G01J 4/04 (2006.01)
B24B 49/00 (2006.01)

(52) U.S. Cl. ........... 356/72; 356/406; 356/369; 250/226
(58) Field of Classification Search ............ 356/72
See application file for complete search history.

(56) References Cited

U.S. PATENT DOCUMENTS

| 6,142,855 A | 11/2000 | Nyui et al. |
| 7,262,849 B2 | 8/2007 | Shima et al. |
| 2001/0036676 A1* | 11/2001 | Mitsuhashi et al. ............. 438/8 |

FOREIGN PATENT DOCUMENTS

| JP | 2005-294365 | * 10/2005 |
| WO | 01/20304 | 3/2001 |
| WO | 01/81902 | 11/2001 |

* cited by examiner

*Primary Examiner* — Fannie L. Evans
(74) *Attorney, Agent, or Firm* — Wenderoth, Lind & Ponack, L.L.P.

(57) ABSTRACT

A polishing end point detection method is to detect a polishing end point of a workpiece having a multilayer structure. The method is performed by emitting a first light and a second light to a surface of the workpiece at a first angle of incidence and a second angle of incidence, respectively, receiving the first light and the second light reflected from the surface through a polarizing filter, performing a first analyzing process of analyzing a brightness and a saturation of the surface from the first light received, performing a second analyzing process of analyzing a brightness and a saturation of the surface from the second light received, and determining removal of the upper layer based on changes in the brightness and the saturation of the surface.

26 Claims, 22 Drawing Sheets

POLISHING END POINT DETECTION METHOD, POLISHING END POINT DETECTION APPARATUS AND POLISHING APPARATUS

BACKGROUND OF THE INVENTION

1. Field of the Invention

The present invention relates to a polishing end point detection method, a polishing end point detection apparatus, and a polishing apparatus, and more particularly to a polishing end point detection method and a polishing end point detection apparatus for detecting an end point of polishing of a multilayer structure.

2. Description of the Related Art

An integrated circuit, which is a semiconductor device, is fabricated through several processes. STI (Shallow Trench Isolation) is one of such fabrication processes, and is important in realizing a finer integrated circuit. STI is a technique of electrically isolating elements, such as transistors, formed on a wafer (typically a silicon wafer) using an insulating film.

FIG. 1 is a cross-sectional view illustrating a process of STI. More specifically, FIG. 1 shows a structure in which a $SiO_2$ film 2 as an insulating film is embedded in grooves (or trenches) formed on a silicon wafer 1. As shown in FIG. 1, a SiN film ($Si_3N_4$) 3 and a thermal oxide pad 4 are formed between a surface of the silicon wafer 1 and the $SiO_2$ film 2. The $SiO_2$ film 2 is polished by CMP (Chemical Mechanical Polishing) until the SiN film 3 is exposed. This SiN film 3 is formed as an underlying layer of the $SiO_2$ film 2. The SiN film 3 functions as a polishing stopper that prevents damage to the surface of the silicon wafer 1 which can be caused by CMP. After CMP, an etching process or the like is performed so as to remove the SiN film 3 and the thermal oxide pad 4 to thereby expose the surface of the silicon wafer 1.

Spectroscopic polishing end point detection has been known as a method of detecting a polishing end point of the $SiO_2$ film 2. This spectroscopic polishing end point detection method monitors an interference color of a surface that is being polished, and detects a polishing end point from a change in the interference color. However, the $SiO_2$ film 2 and the underlying SiN film 3 have a similar index of refraction, and as a result, the interference colors thereof are similar to each other. Therefore, it is difficult to detect the polishing end point from the change in the interference color using the spectroscopic polishing end point detection method.

A method using a laser light is also known as a method of detecting the polishing end point of the $SiO_2$ film 2. This method directs the laser light to a surface of a film, and detects the polishing end point from a change in intensity of the laser light reflected from the film. However, this method has the following problems. Since the laser light is a monochromatic light, the reflected laser light disappears periodically as a thickness of the film changes. This is because a condition of interference between the laser light reflected from the surface of the film and the laser light that has passed through the film and has been reflected from a surface of an underlayer changes depending on the thickness of the film. Such a periodical change in intensity of the laser light prevents accurate detection of the polishing end point. Moreover, since circuit patterns are generally formed on the surface of the wafer, the highly-directional laser light may be reflected at an unexpected angle due to an effect of the circuit patterns. As a result, the reflected laser light cannot be received.

Ellipsometry (polarization analysis) is also known as a method of detecting a polishing end point of a film. This ellipsometry is a technique of determining an index of refraction and a thickness of a film. Ellipsometry applies a linearly-polarized light to a film on a substrate, and measures a phase difference $\Delta$ between p-polarized light and s-polarized light in the reflected light from the film and an amplitude ratio $\psi$ of the p-polarized light to the s-polarized light. The index of refraction and the thickness of the film are determined from the measurements $\Delta$ and $\psi$.

The index of refraction and the thickness of the film cannot be calculated directly from the measurements $\Delta$ and $\psi$. Thus, in ellipsometry, an optical model is prepared in advance, and the index of refraction and the thickness are analyzed using a curve fitting or other technique. However, analyzing of the index of refraction and the thickness of the film is complex. Therefore, a relatively long period of time is required for determining the film thickness. The polishing end point detecting function of the polishing apparatus exerts a great influence on quality of a polished workpiece. In particular, it is strictly required to prevent excess polishing. In order to prevent excess polishing, it is necessary to measure a state of the film and to quickly determine the polishing end point (e.g., a point where the underlying film is exposed) so as to stop polishing.

SUMMARY OF THE INVENTION

The present invention has been made in view of the above drawbacks. It is therefore a first object of the present invention to provide a polishing end point detection method and a polishing end point detection apparatus capable of accurately detecting a polishing end point of a workpiece having a multilayer structure.

It is a second object of the present invention to provide a polishing end point detection method and a polishing apparatus capable of quickly detecting a polishing end point utilizing ellipsometry, without performing complex analyzing of a film thickness and an index of refraction.

In order to achieve the above object, one aspect of the present invention provides a method of detecting a polishing end point of a workpiece having an upper layer and an underlying lower layer. This method includes emitting a first light and a second light to a surface of the workpiece at a first angle of incidence and a second angle of incidence, respectively, receiving the first light and the second light reflected from the surface through a polarizing filter, performing a first analyzing process of analyzing a brightness and a saturation of the surface from the first light received, performing a second analyzing process of analyzing a brightness and a saturation of the surface from the second light received, and determining removal of the upper layer based on changes in the brightness and the saturation of the surface.

In a preferred aspect of the present invention, the first angle of incidence is an angle selected from a range of a first Brewster's angle ±10 degrees, the first Brewster's angle depending on the upper layer, and the second angle of incidence is an angle selected from a range of a second Brewster's angle ±10 degrees, the second Brewster's angle depending on the lower layer.

In a preferred aspect of the present invention, the determining of removal of the upper layer comprises determining removal of the upper layer by detecting an abrupt changes in the brightness and the saturation of the surface analyzed from at least one of the first light and the second light.

In a preferred aspect of the present invention, the determining of removal of the upper layer comprises determining removal of the upper layer by detecting that the brightness and the saturation of the surface analyzed from the first light exceed the brightness and the saturation of the surface analyzed from the second light.

In a preferred aspect of the present invention, each of the first analyzing process and the second analyzing process includes decomposing a color of the surface into a R component, a G component, and a B component, and quantifying the brightness and the saturation of the surface from the R component, the G component, and the B component.

In a preferred aspect of the present invention, each of the first analyzing process and the second analyzing process further includes obtaining a R value, a G value, and a B value representing the quantified R component, the G component, and the B component, respectively, calculating a RGB assessment value which is an average, a root mean square, variance, or standard deviation of the R value, the G value, and the B value, or a value given by multiplying the R value, the G value, and the B value by predetermined coefficients, respectively, and summing the resultant values, and defining the RGB assessment value as the brightness of the surface.

In a preferred aspect of the present invention, each of the first analyzing process and the second analyzing process further includes calculating a difference between the R value, the G value, and the B value, and defining the difference as the saturation of the surface.

Another aspect of the present invention is to provide an apparatus for detecting a polishing end point of a workpiece having an upper layer and an underlying lower layer. This apparatus includes a light emitter configured to emit a first light and a second light to a surface of the workpiece at a first angle of incidence and a second angle of incidence, respectively, a light receiver configured to receive the first light and the second light reflected from the surface, a polarizing filter located between the surface of the workpiece and the light receiver, and a processing section configured to perform a first analyzing process of analyzing a brightness and a saturation of the surface from the first light received by the light receiver and to perform a second analyzing process of analyzing a brightness and a saturation of the surface from the second light received by the light receiver. The processing section is configured to determine removal of the upper layer based on changes in the brightness and the saturation of the surface.

Another aspect of the present invention is to provide an apparatus for polishing a workpiece having an upper layer and an underlying lower layer. The apparatus includes a polishing table configured to support a polishing pad having the polishing surface and a through-hole, a top ring configured to press the workpiece against the polishing surface of the polishing pad, and a polishing end point detection unit. The polishing end point detection unit includes (i) a light emitter configured to emit a first light and a second light through the through-hole to a surface of the workpiece at a first angle of incidence and a second angle of incidence, respectively, (ii) a light receiver configured to receive the first light and the second light reflected from the surface, (iii) a polarizing filter located between the surface of the workpiece and the light receiver, and (iv) a processing section configured to perform a first analyzing process of analyzing a brightness and a saturation of the surface from the first light received and to perform a second analyzing process of analyzing a brightness and a saturation of the surface from the second light received. The processing section is configured to determine removal of the upper layer based on changes in the brightness and the saturation of the surface.

Another aspect of the present invention is to provide a method of detecting a polishing end point of a workpiece. This method includes emitting a light to a surface of the workpiece, receiving the light reflected from the surface of the workpiece, obtaining a phase difference $\Delta$ between p-polarized light and s-polarized light contained in the reflected light and an amplitude ratio $\psi$ of the p-polarized light to the s-polarized light, plotting coordinates, specified by the amplitude ratio $\psi$ and the phase difference $\Delta$, on a coordinate system having coordinate axes representing the amplitude ratio $\psi$ and the phase difference $\Delta$, and determining the polishing end point based on a change in track of the coordinates plotted on the coordinate system.

In a preferred aspect of the present invention, the determining of the polishing end point comprises obtaining in advance a regularity of the track of the coordinates, and determining the polishing end point based on the regularity.

In a preferred aspect of the present invention, determining of the polishing end point based on the regularity comprises determining the polishing end point by detecting deviation of the track from the regularity.

In a preferred aspect of the present invention, the determining of the polishing end point comprises determining the polishing end point by detecting a time point when the coordinates exceed a predetermined range or threshold.

Another aspect of the present invention is to provide a method of detecting a polishing end point of a workpiece. The method includes emitting a light to a surface of the workpiece, receiving the light reflected from the surface of the workpiece, obtaining a phase difference $\Delta$ between p-polarized light and s-polarized light contained in the reflected light, plotting coordinates, specified by a polishing time t and the phase difference $\Delta$, on a coordinate system having coordinate axes representing the polishing time t and the phase difference $\Delta$, and determining the polishing end point based on a change in track of the coordinates plotted on the coordinate system.

Another aspect of the present invention is to provide a method of detecting a polishing end point of a workpiece. This method includes emitting a light to a surface of the workpiece, receiving the light reflected from the surface of the workpiece, obtaining an amplitude ratio $\psi$ of p-polarized light to s-polarized light contained in the reflected light, plotting coordinates, specified by a polishing time t and the amplitude ratio $\psi$, onto a coordinate system having coordinate axes representing the polishing time t and the amplitude ratio $\psi$, and determining the polishing end point based on a change in track of the coordinates plotted on the coordinate system.

Another aspect of the present invention is to provide an apparatus for polishing a workpiece by providing relative motion between the workpiece and a polishing surface. This apparatus includes a polishing table configured to support a polishing pad having the polishing surface and a through-hole, an upper end of the through-hole lying in the polishing surface, a top ring configured to press the workpiece against the polishing surface of the polishing pad, a light emitter configured to emit a light to a surface of the workpiece through the through-hole, a light receiver configured to receive the light from the workpiece, a calculating section configured to obtain a phase difference $\Delta$ between p-polarized light and s-polarized light contained in the reflected light and an amplitude ratio $\psi$ of the p-polarized light to the s-polarized light, a determining section configured to plot coordinates, specified by the amplitude ratio $\psi$ and the phase difference $\Delta$, on a coordinate system having coordinate axes representing the amplitude ratio $\psi$ and the phase difference $\Delta$ and to determine a polishing end point based on a change in track of the coordinates plotted on the coordinate system, and a controller configured to control polishing of the workpiece.

In a preferred aspect of the present invention, the apparatus further includes at least one polarizer located in an optical path connecting between the light receiver and the workpiece.

In a preferred aspect of the present invention, the at least one polarizer comprises a first polarizer arranged at an angle of 0 degree with respect to a plane of incidence, a second polarizer arranged at an angle of 90 degrees with respect to the plane of incidence, and at least one polarizer arranged at an angle differing from the angles of the first polarizer and the second polarizer.

In a preferred aspect of the present invention, the at least one polarizer arranged at an angle differing from the angles of the first polarizer and the second polarizer comprises a third polarizer arranged at an angle of 45 degrees with respect to the plane of incidence and a fourth polarizer arranged at an angle of 135 degrees with respect to the plane of incidence, and the calculating section is configured to calculate the phase difference $\Delta$ and the amplitude ratio $\psi$ from intensities of the reflected light that has passed through the first polarizer, the second polarizer, the third polarizer, and the fourth polarizer.

In a preferred aspect of the present invention, the light receiver comprises four photodetectors, and four optical fibers having one ends coupled to the four photodetectors and other ends located adjacent to the surface of the workpiece. The first polarizer, the second polarizer, the third polarizer, and the fourth polarizer are mounted on the other ends of the four photodetectors.

In a preferred aspect of the present invention, the light emitter has a light source configured to emit a white light, and a spectral filter is provided between the four optical fibers and the four photodetectors.

In a preferred aspect of the present invention, an angle of incidence of the light is in a range of a Brewster's angle $\pm 10$ degrees, the Brewster's angle depending on the workpiece.

In a preferred aspect of the present invention, the light receiver has an image sensor.

In a preferred aspect of the present invention, a polarizer is attached to a front surface of each pixel of the image sensor.

In a preferred aspect of the present invention, the light emitter comprises multiple light sources configured to emit multiple lights having different wavelengths.

In a preferred aspect of the present invention, the light emitter comprises a pulsed light emitter.

In a preferred aspect of the present invention, the controller is configured to stop polishing of the workpiece after a predetermined time has elapsed since the determining section has determined the polishing end point.

According to one aspect of the present invention, because the brightness and the saturation of the surface decrease or increase abruptly at the polishing end point (i.e., when the upper layer is removed), the polishing end point can be detected accurately based on the changes in the brightness and the saturation of the surface that is being polished.

According to another aspect of the present invention, because the polishing end point is determined by monitoring the change in at least one of the phase difference $\Delta$ and the amplitude ratio $\psi$, it is not necessary to analyze the film thickness and the index of refraction. Therefore, the polishing end point can be quickly detected.

DETAILED DESCRIPTION OF THE PREFERRED EMBODIMENTS

Embodiments of the present invention will be described below with reference to the drawings.

The principle of the present invention will now be described with reference to FIG. 2. When a light is incident on an interface between two substances having different indexes of refraction, p-polarized light is not reflected from the interface at a particular angle of incidence. This angle of incidence is called Brewster's angle, which is given by a known formula using the indexes of refraction of the two substances. FIG. 3 is a graph illustrating a reflectance of p-polarized light and a reflectance of s-polarized light that vary depending on the angle of incidence. As shown in FIG. 3, Brewster's angle given by indexes of refraction of air and $SiO_2$ is 55.4 degrees, and Brewster's angle given by indexes of refraction of air and SiN is 63.4 degrees.

Figure 2:
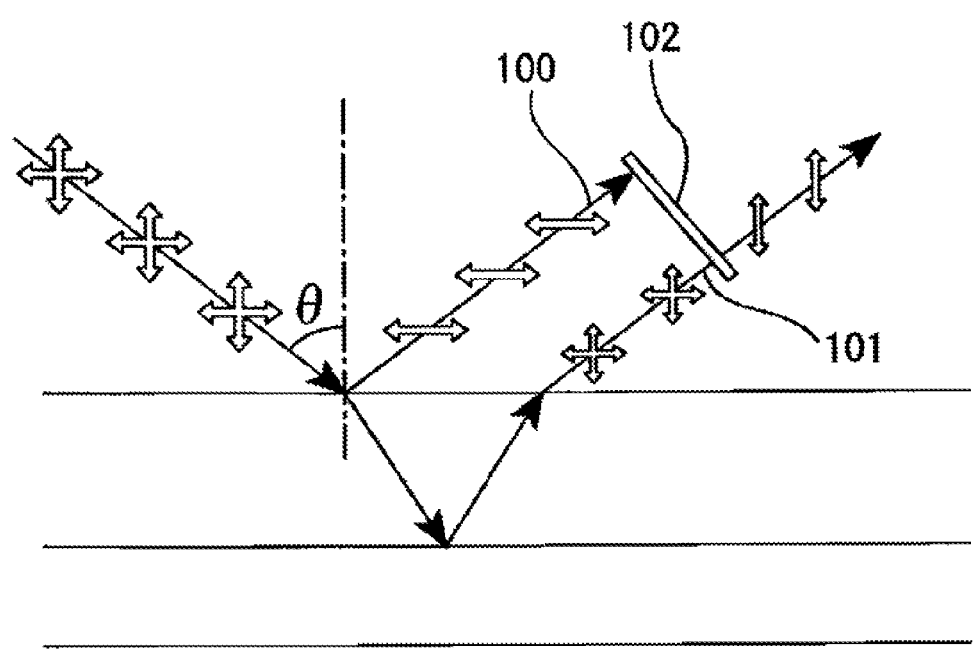
FIG. 2 is a view for illustrating a principle of a polishing end point detection according to an embodiment of the present invention.
Figure 3:
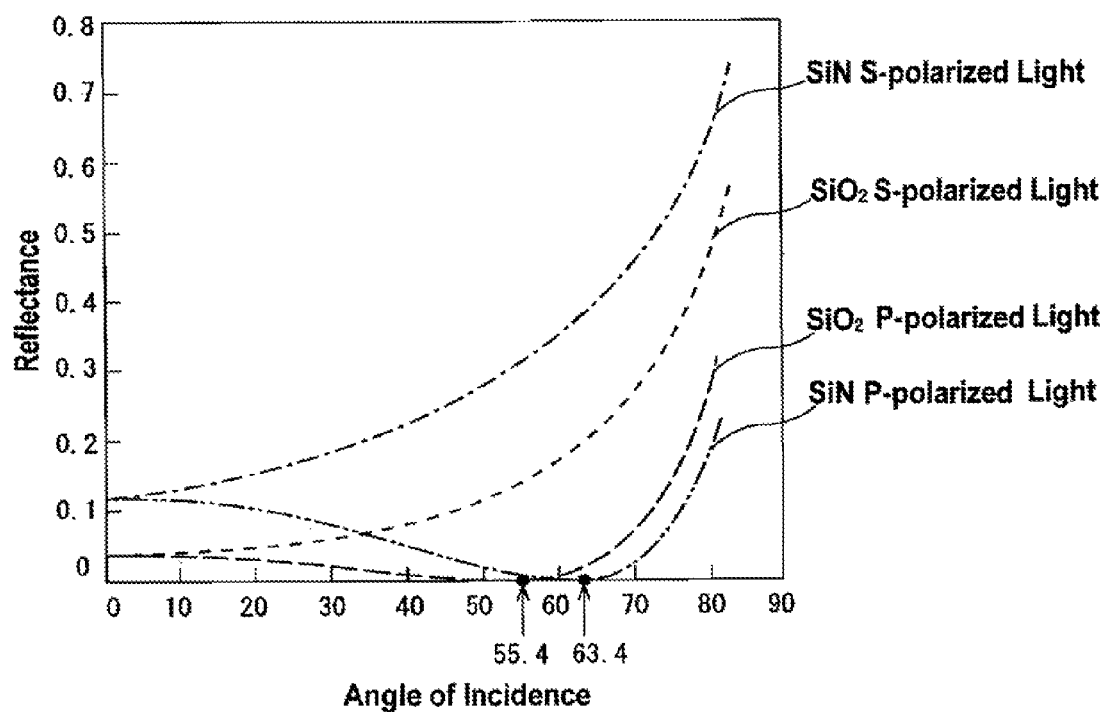
FIG. 3 is a graph illustrating a reflectance of p-polarized light and a reflectance of s-polarized light that vary depending on an angle of incidence.

In FIG. 2, when the light is incident on the interface at an angle near the Brewster's angle θ, the reflected light is mainly composed of the s-polarized light (this reflected light is denoted by reference numeral 100 in FIG. 2). Part of the incident light passes through a substance (e.g., a film), and is reflected off a surface of an underlayer (this reflected light is denoted by reference numeral 101 in FIG. 2). The reflected light 100 and the reflected light 101 interfere with each other to produce an interference color.

When a polarizing filter 102, which is configured to remove the s-polarized light, is placed in an optical path of the reflected light 100 and the reflected light 101 as shown in FIG. 2, the reflected light 100 is substantially cut off by the polarizing filter 102 because the reflected light 100 is composed of substantially only the s-polarized light. On the other hand, the s-polarized light contained in the reflected light 101 is cut off by the polarizing filter 102, and only the p-polarized light passes. In this state, the reflected light 100 and the reflected light 101 hardly interfere with each other. As a result, the interference color that is observed through the polarizing filter 102 is thin, and the reflected light that has passed through the polarizing filter 102 is dim.

Using such physical phenomenon, the method and apparatus according to the present invention detect the polishing end point. More specifically, the polishing end point detection according to the present invention is performed by directing the first light and the second light to the surface at the Brewster's angles that depend on the upper layer and the lower layer (or at angles selected from a range of the Brewster's angles −10° to the Brewster's angles +10°); monitoring the brightness and the saturation of the surface through the polarizing filter provided in the path of the reflected first light and the second light; and detecting abrupt decrease or increase in the brightness and the saturation of the surface. The removal of the upper layer can be determined by detecting the abrupt decrease or increase in the brightness and the saturation of the surface. The light to be directed to the surface may be a light containing the above-mentioned a first light and a second light. For example, a light having a certain cross section may be projected onto the surface at an angle of at least 50 degrees with respect to a perpendicular of the surface that is being polished, and the reflected light from the surface may be sorted into predetermined plural zones which are defined as a first light, a second light, . . . , and so forth.

Figure 4:
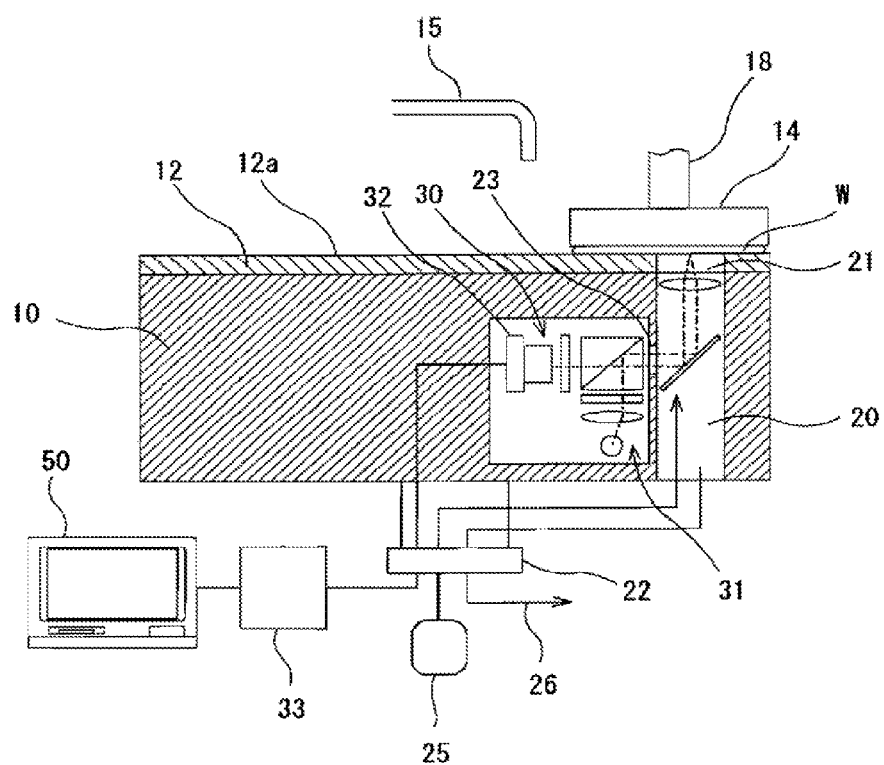
FIG. 4 is a schematic view showing an entire structure of a polishing apparatus according to an embodiment of the present invention.

FIG. 4 is a schematic view showing an entire structure of a polishing apparatus according to an embodiment of the present invention. As shown in FIG. 4, the polishing apparatus includes a polishing table 10, a polishing pad 12 attached to an upper surface of the polishing table 10, a top ring 14 configured to hold a substrate W (i.e., a workpiece to be polished) and to press the substrate W against the polishing pad 12, and a polishing liquid supply nozzle 15 configured to supply a polishing liquid (slurry) onto the polishing pad 12. The polishing table 10 is coupled to a motor (not shown in the drawing) provided below the polishing table 10, so that the polishing table 10 is rotated about its own axis.

Figure 1:
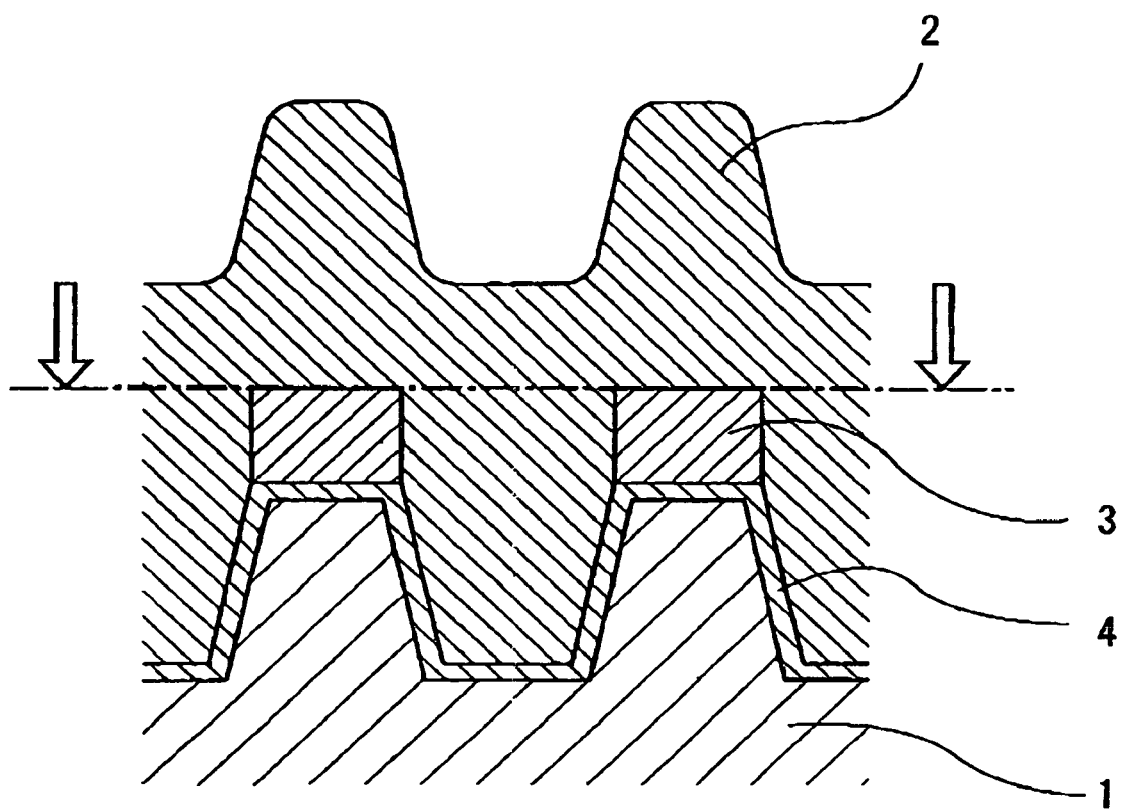
FIG. 1 is a cross-sectional view showing a process of STI.

The polishing pad 12 has an upper surface 12a, which provides a polishing surface where the substrate W is polished as a result of sliding contact with the polishing surface. The substrate W has, as shown in FIG. 1, a SiN film and a $SiO_2$ film formed on the SiN film. Both the $SiO_2$ film and the SiN film are an insulating film. While the following descriptions are about an example of polishing a substrate having the $SiO_2$ film and the SiN film which are an upper layer and a lower layer, the present invention can be applied to processes of polishing an insulating film other than the $SiO_2$ film and the SiN film.

The top ring 14 is coupled to a motor and an elevating cylinder (not shown in the drawing) via a top ring shaft 18. This configuration allows the top ring 14 to move vertically and to rotate about the top ring shaft 18. The top ring 14 has a lower surface which is configured to hold the substrate W by a vacuum suction or the like.

The substrate W, held on the lower surface of the top ring 14, is rotated by the top ring 14, and is pressed against the polishing pad 12 on the rotating polishing table 10. During the sliding contact between the substrate W and the polishing pad 12, the polishing liquid is supplied onto the polishing surface 12a of the polishing pad 12 from the polishing liquid supply nozzle 15. In this manner, a surface (i.e., a lower surface) of the substrate W is polished with the polishing liquid being present between the surface of the substrate W and the polishing pad 12. In this embodiment, a mechanism of providing relative motion between the substrate W and the polishing pad 12 is constructed by the polishing table 10 and the top ring 14.

The polishing table 10 has a hole 20 which has an upper end lying in the upper surface of the polishing table 10. The polishing pad 12 has a through-hole 21 at a position corresponding to the hole 20. The hole 20 and the through-hole 21 are in fluid communication with each other. The hole 20 is coupled to a liquid supply source 25 and a discharge passage 26 via a rotary joint 22. The liquid supply source 25 is configured to supply pure water (i.e., a transparent liquid) into the hole 20. The pure water fills a space formed by the lower surface (rear surface) of the substrate W and the through-hole 21, and is then expelled therefrom through the discharge passage 26.

The polishing apparatus has a polishing end point detection unit 30 for detecting a polishing end point of the substrate W. This polishing end point detection unit 30 includes a light emitter 31 configured to emit a light (preferably a white light) to the substrate W, and a CCD camera 32 as a light receiver configured to receive the light reflected from the substrate W. The CCD camera 32 is an imaging device configured to receive the light reflected off the surface of the substrate W and to create an image of the surface that is being polished. The light receiver may be an imaging device using an image sensor (e.g., CMOS) or may be a spectroscope. The light emitter 31 and the CCD camera 32 are disposed in the polishing table 10. The polishing end point detection unit 30 further includes a processing section 33 configured to analyze the image obtained by the CCD camera 32.

Figure 5:
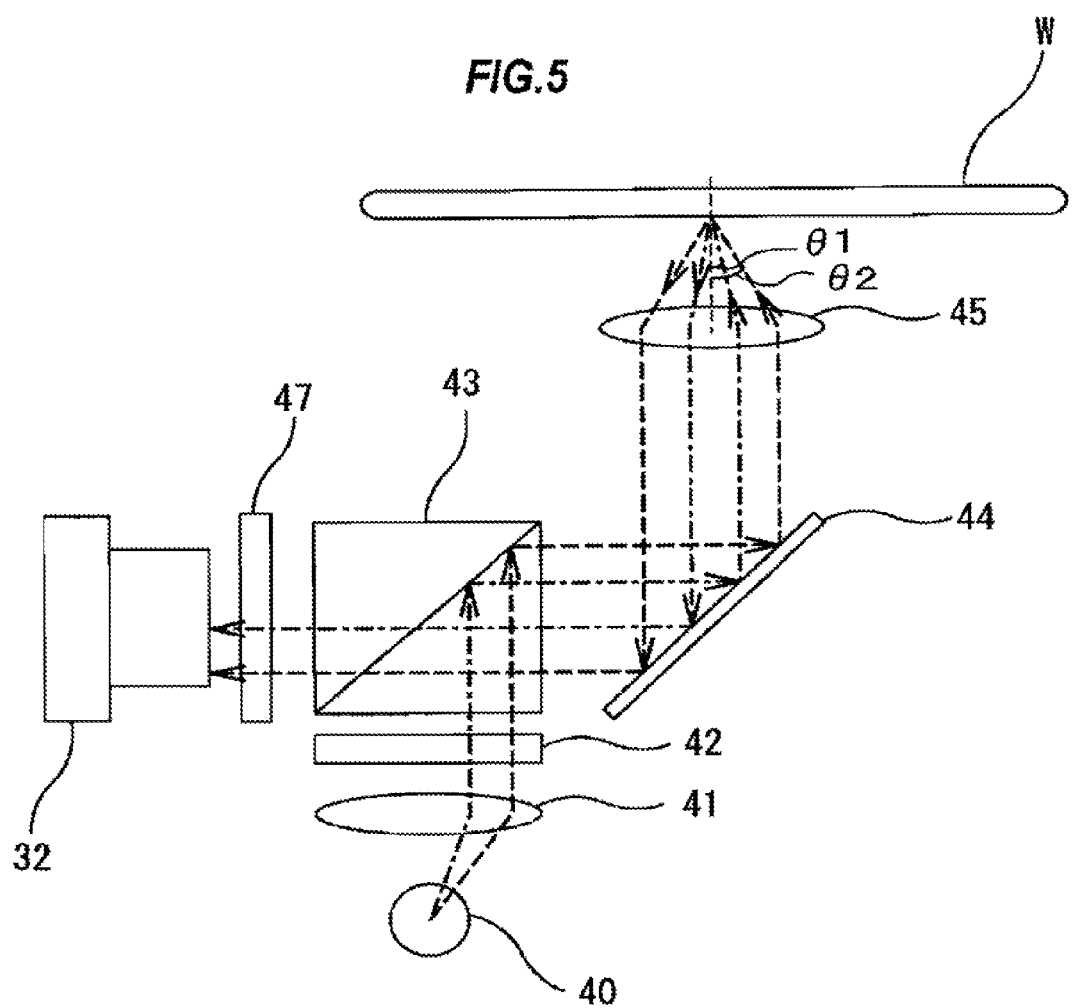
FIG. 5 is an enlarged view showing a light emitter of a polishing end point detection unit.

FIG. 5 is an enlarged view showing the light emitter 31 of the polishing end point detection unit 30. As shown in FIG. 5, the light emitter 31 includes a light source 40, a first lens 41 configured to convert a spreading light emitted by the light source 40 into a parallel light (a flux of multiple lights traveling parallel to each other), and a polarizing filter 42 configured to polarize the parallel light that has passed through the first lens 41. This polarizing filter 42 is provided so as to adjust the parallel light such that the parallel light contains p-polarized light and s-polarized light equally. Specifically, the parallel light is converted by the polarizing filter 42 into light polarized at 45 degrees.

The light emitter 31 further includes a beam splitter 43, a reflector 44, and a second lens 45. The reflector 44 and the second lens 45 are arranged in the hole 20 (see FIG. 4). Part of the parallel light, polarized by passing through the polarizing filter 42, is changed in its traveling direction by the beam splitter 43 and the reflector 44 so as to pass through the second lens 45, and is incident on the substrate W on the polishing pad 12. The second lens 45 is a convergent lens configured to focus the parallel light on a point on the surface of the substrate W. The reflect light from the substrate W is converted into the parallel light again by the second lens 45. This parallel light is received by the CCD camera 32 via the reflector 44 and the beam splitter 43. A polarizing filter 47 is disposed in front of the CCD camera 32. This polarizing filter 47 is configured to adjust a polarization direction of the light that is incident on the CCD camera 32. In this embodiment, the polarizing filter 47 is configured to cut off (or remove) the s-polarized light.

As shown in FIG. 4, part of a side wall of the hole 20 formed in the polishing table 10 is constituted by a transparent window (e.g., a transparent acryl) 23. This transparent window 23 is provided for preventing the pure water in the hole 20 from leaking out while allowing the light to travel. The CCD camera 32 is coupled to the processing section 33, and the image, obtained by the CCD camera 32, is sent to the processing section 33. The processing section 33 analyzes the image and quantifies a brightness and a saturation of the surface of the substrate W that is being polished. Further, the processing section 33 detects a polishing end point from the quantified brightness and saturation. The processing section 33 sends a signal indicating the detection of the polishing end point to a controller 50. The controller 50 receives this signal and stops the polishing operation of the polishing apparatus.

The second lens 45 establishes an angle of incidence of the light converging on the point on the surface of the substrate W. In this embodiment, a range of the angle of incidence is from 0 to 70 degrees. Therefore, this range of angle of incidence includes 55.4 degrees (which will be hereinafter referred to as a first angle $\theta 1$) and 63.4 degrees (which will be hereinafter referred to as a second angle $\theta 2$). The first angle $\theta 1$ (55.4 degrees) is the Brewster's angle in a case where the light travels through the air to impinge upon the $SiO_2$ film. The second angle $\theta 2$ (63.4 degrees) is the Brewster's angle in a case where the light travels through the air to impinge upon the SiN film. Therefore, the light, emitted from the light emitter 31, contains a first light that is incident on the surface of the substrate W at the first angle $\theta 1$ and a second light that is incident on the surface of the substrate W at the second angle $\theta 2$.

The above-mentioned Brewster's angles are those in the case where $SiO_2$ and SiN contact the air. On the other hand, when $SiO_2$ and SiN contact a liquid, the Brewster's angles vary. For example, when the optical path is filled with the water as shown in FIG. 4, the Brewster's angle $\theta 1$ of $SiO_2$ is 47.5 degrees and the Brewster's angle $\theta 2$ of SiN is 56.4 degrees.

Figure 6:
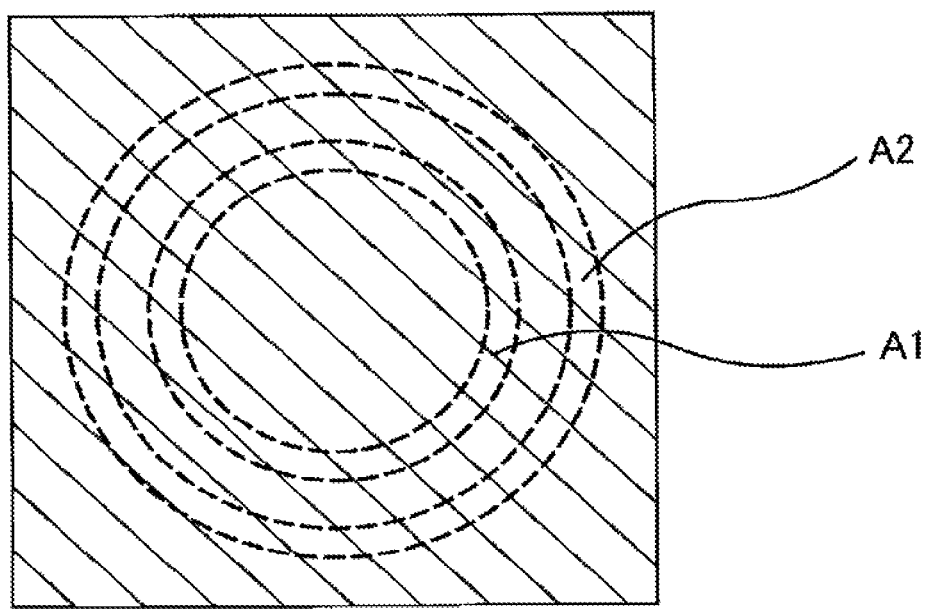
FIG. 6 is a schematic view illustrating an image obtained by a CCD camera.

FIG. 6 is a schematic view illustrating an image obtained by the CCD camera 32. In FIG. 6, a symbol A1 indicates a first region corresponding to the first angle $\theta 1$ which is the Brewster's angle of $SiO_2$ and a symbol A2 indicates a second region corresponding to the second angle $\theta 2$ which is the Brewster's angle of SiN. At an initial stage of polishing, the exposed surface of the substrate W is constituted by the $SiO_2$ film. Therefore, for the reasons as discussed with reference to FIG. 2, the brightness and the saturation in the first region A1 are low (in other words, the region A1 is of nearly gray and is dark). On the other hand, in the other regions including the second region A2, the brightness and the saturation are high as compared with the first region A1 (in other words, the region A2 is colorful and bright).

When polishing proceeds to remove the $SiO_2$ film, the brightness and the saturation in the first region A1 become abruptly high. On the other hand, the brightness and the saturation in the second region A2 become abruptly low because the SiN film is exposed. The processing section 33 analyzes the image sent from the CCD camera 32, quantifies the brightness and the saturation in the first region A1 and the second region A2, and detects the abrupt changes in the brightness and the saturation in at least one of the first region A1 and the second region A2 to thereby determine the polishing end point. Preferably, the processing section 33 determines the polishing end point by detecting that the brightness and the saturation of the first region A1 exceed the brightness and the saturation of the second region A2.

Figure 7:
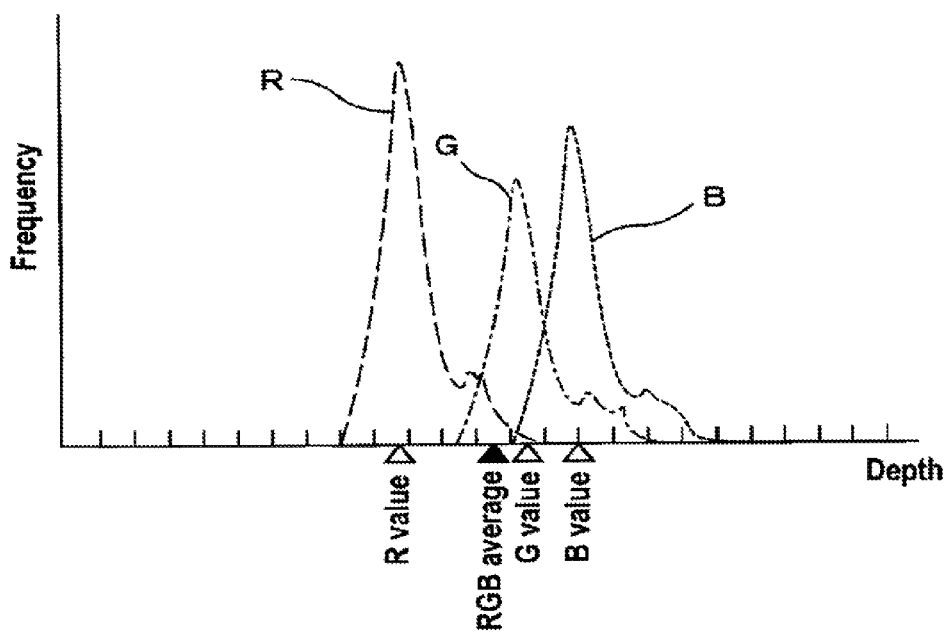
FIG. 7 is a diagram showing a RGB histogram.

Quantification of the brightness and the saturation of the image is performed as follows. The processing section 33 creates a RGB histogram with respect to the first region A1 (i.e., the region corresponding to the first angle $\theta 1$ as the Brewster's angle of $SiO_2$) and a RGB histogram with respect to the second region A2 (i.e., the region corresponding to the second angle $\theta 2$ as the Brewster's angle of SiN). FIG. 7 is a diagram showing the RGB histogram. As shown in FIG. 7, the RGB histogram has a horizontal axis indicating a depth of a color and a vertical axis indicating a frequency (i.e., the number of pixels).

The processing section 33 decomposes the color of the first region A1 and the second region A2 into a R (red) component, a G (green) component, and a B (blue) component, and creates graphs each indicating relationship between the depth (strength) of each component (the R component, G component, B component) and the number of pixels having that depth, as shown in FIG. 7. The processing section 33 calculates centroids of the R component, the G component, and the B component, respectively, to thereby quantify the R component, the G component, and the B component. Hereinafter, the quantified values of the R component, the G component, and the B component will be referred to as an R value, a G value, and a B value, respectively. The R value, the G value, and the B value may be respective peak values of the depth (strength) of the R component, the G component, and the B component, or may be areas of the R component, the G component, and the B component. Each area can be the total number of pixels having each component.

Further, the processing section 33 calculates an average of the R value, the G value, and the B value (hereinafter, this average will be referred to as a RGB assessment value). This RGB assessment value varies depending on the brightness of the image. Therefore, the processing section 33 defines the RGB assessment value as the brightness of the surface of the substrate W, and monitors the RGB assessment value during polishing. Other than the average of the R value, the G value, and the B value, the RGB assessment value may be a root mean square, variance, or standard deviation of the R value, the G value, and the B value, or may be a value given by multiplying the R value, the G value, and the B value by predetermined coefficients, respectively, and summing the resultant values.

The processing section 33 further calculates a difference between the R value, the G value, and the B value (which will be referred to as a RGB difference), and defines this RGB difference as an index indicating the saturation of the surface of the substrate W. Specifically, the RGB difference is calculated by using the following formula.

$$(R\text{ value}-G\text{ value})^2+(R\text{ value}-B\text{ value})^2+(G\text{ value}-B\text{ value})^2$$

The RGB difference, given by the above formula, varies depending on the saturation of the image. More specifically, when the saturation of the image is lowered, the RGB difference is also lowered, and when the saturation of the image is increased, the RGB difference is also increased. In this manner, the processing section 33 quantifies the brightness and the saturation of the first region A1 and the second region A2. Instead of the above-mentioned RGB difference, standard deviation may be used as the index of the saturation.

Figure 8:
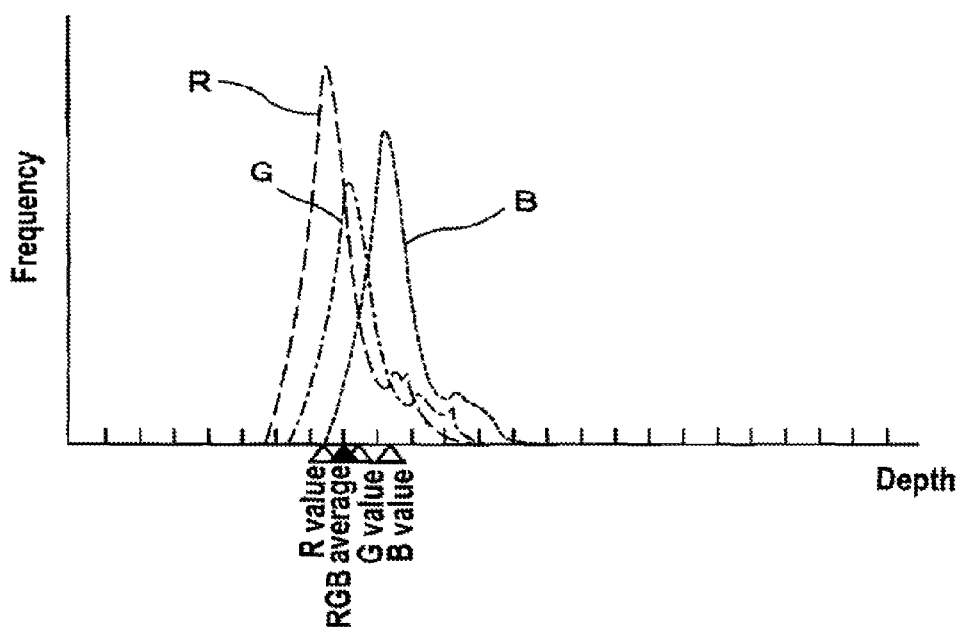
FIG. 8 is a diagram showing a RGB histogram created by analyzing an image obtained while the light is incident at Brewster's angle.

FIG. 8 is a diagram showing the RGB histogram created by analyzing an image obtained while the light is incident at the Brewster's angle. As shown in FIG. 8, an image with low brightness and low saturation has low values in the R component, the G component, and the B component in their entirety, and exhibits a narrow width of each component as a whole. As a result, the RGB assessment value and the RGB difference indicating the brightness and the saturation of the image become low.

The processing section 33 monitors the RGB assessment value (i.e., the brightness) and the RGB difference (i.e., the saturation) of the first region A1 and the RGB assessment value (i.e., the brightness) and the RGB difference (i.e., the saturation) of the second region A2 during polishing. Abrupt changes in the RGB assessment value and the RGB difference of one of the first region A1 and the second region A2 mean the removal of the $SiO_2$ film or the exposure of the SiN film. Therefore, the removal of the $SiO_2$ film can be determined by detecting the abrupt changes in the RGB assessment value and the RGB difference (i.e., the brightness and the saturation) of one of the first region A1 and the second region A2. Preferably, the processing section 33 determines the polishing end point by detecting a time point when the brightness and the saturation of the first region A1 exceed the brightness and the saturation of the second region A2. The detection of the abrupt changes in the RGB assessment value and the RGB difference can be performed by, for example, differentiating the RGB assessment value and the RGB difference and determining whether the resultant values, obtained by the differentiation, exceed predetermined respective thresholds.

The color of the surface of the substrate changes depending on a thickness of a film. This is because a degree of interference between the light reflected from the surface of the film and the light that has passed through the film and has been reflected from a surface of an underlying material changes depending on the thickness of the film. The color of the surface of the substrate also changes depending on circuit patterns. Moreover, films with similar indexes of refraction have colors similar to each other. Accordingly, it is difficult to detect the polishing end point based on an absolute change in color. In this embodiment, instead of the absolute change in color, relative changes in brightness and saturation are monitored. Therefore, according to the embodiment of the present invention, an accurate polishing end point can be detected without being affected by the film thickness, the index of refraction, and the circuit patterns.

The first angle $\theta 1$ can be selected from a range of the Brewster's angle of $SiO_2$ ±10 degrees, preferably from a range of the Brewster's angle of $SiO_2$ ±5 degrees. Similarly, the second angle $\theta 2$ can be selected from a range of the Brewster's angle of SiN ±10 degrees, preferably from a range of the Brewster's angle of SiN ±5 degrees. Even when the angles $\theta 1$ and $\theta 2$ are selected from the range determined from the Brewster's angle ±10 degrees, it is possible to recognize the changes in the two lights (i.e., the changes in the brightness and the saturation of the surface).

In order to acquire a clear image, it is preferable to pass the pure water through the hole 20 and the through-hole 21 during polishing. The polishing liquid (e.g., slurry), mixed into the pure water, is removed together with the pure water. Further, because the pure water fills the optical path, the pure water can prevent noise generation, which would be caused by infraction and scattering of the light, and can therefore prevent an adverse influence on information about the surface that is being polished. In addition, the pure water can prevent a decrease in quantity of light. If the polishing pad has a transparent window through which the light passes, the light travels through the air and the window in this order to the surface of the substrate, and the reflected light travels through the window and the air again. As a result, infraction and scattering of the light could occur at interfaces therebetween. In this embodiment, only an interface between the pure water and the substrate exists. Therefore, infraction and scattering of the light can be prevented.

In this embodiment, it is possible to provide a discharge hole adjacent to the hole 20, so that supply of the pure water (i.e., transparent liquid) and discharge of the pure water can be performed independently. Depending on a type of polishing liquid, it is possible to close a lower end of the hole 20 with a transparent lid (e.g., acryl) so that the pure water is retained in the hole 20 and the through-hole 21.

Figure 9:
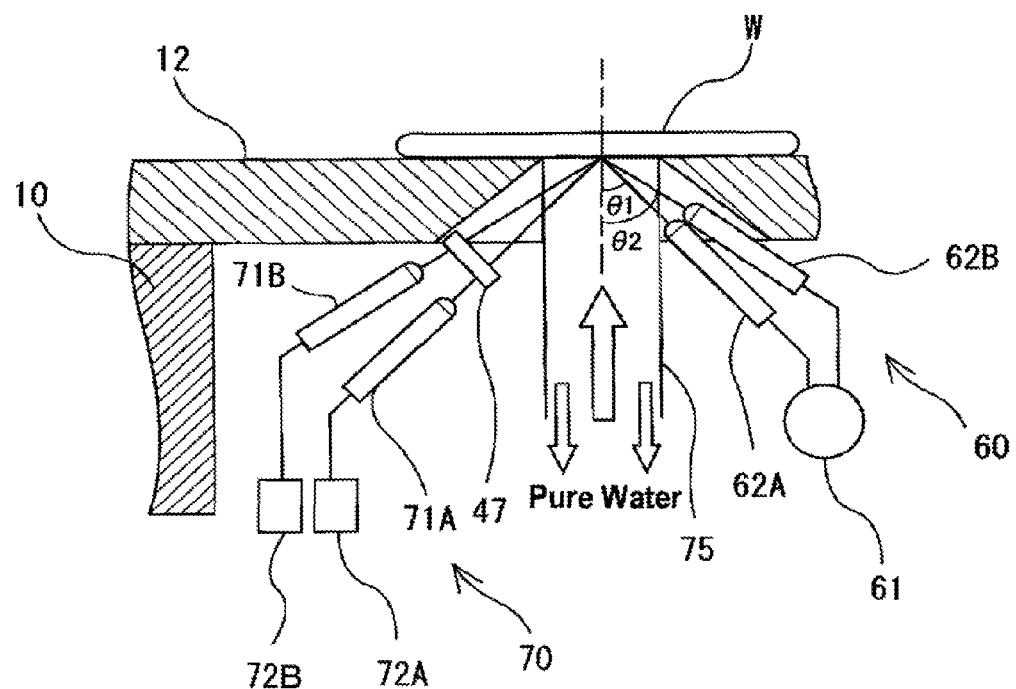
FIG. 9 is a view showing part of the polishing end point detection unit according to another embodiment of the present invention.

FIG. 9 is a view showing part of the polishing end point detection unit according to another embodiment of the present invention. Structures and operations of the polishing end point detection unit and the polishing apparatus of this embodiment, which are identical to those of the first embodiment, will not be described repetitively.

As shown in FIG. 9, a light emitter 60 includes a light source 61 configured to emit a light (preferably a white light), a first light-emitting optical fiber 62A configured to direct a first light to the surface of the substrate at the first angle $\theta 1$, and a second light-emitting optical fiber 62B configured to direct a second light to the surface of the substrate at the second angle $\theta 2$. The first light-emitting optical fiber 62A and the second light-emitting optical fiber 62B are coupled to the light source 61. It is preferable to provide in front of the optical fibers 62A and 62B a polarizing filter configured to polarize the light at an angle of 45 degrees.

A light receiver 70 includes a first light-receiving optical fiber 71A and a second light-receiving optical fiber 71B arranged at angles corresponding respectively to angles of reflection of the first light and the second light. The light receiver 70 further includes a first light-quantity detector (light-receiving device) 72A and a second light-quantity detector (light-receiving device) 72B configured to receive the first light and the second light via the first light-receiving optical fiber 71A and the second light-receiving optical fiber 71B, respectively. The light-receiving device may be an imaging device (photodetector) using an image sensor (e.g., CMOS) or may be a spectroscope. Polarizing filter 47 is disposed between the light-receiving optical fibers 71A and 71B and the substrate W. This polarizing filter 47 is configured to cut off (or remove) the s-polarized light.

A conduit 75 is provided in polishing table 10 and polishing pad 12. This conduit 75 is made of a transparent material, such as acryl, and has a light transmission capability. An upper end of the conduit 75 is located slightly below the polishing surface. The conduit 75 has a circular or rectangular horizontal cross section. Liquid supply source 25 and discharge passage 26, shown in FIG. 4, are coupled to the conduit 75. The light-emitting optical fibers 62A and 62B and the light-receiving optical fibers 71A and 71B are arranged on both sides of the conduit 75.

The two light-quantity detectors 72A and 72B are coupled to processing section 33 shown in FIG. 4. The processing section 33 analyzes the brightness and the saturation of the surface of the substrate from two images obtained respectively by the light-quantity detectors 72A and 72B. These two images correspond to the first region A1 and the second region A2 in the first embodiment. Therefore, the processing section 33 can detect the polishing end point in the same process of the first embodiment by monitoring the brightness and the saturation of the surface shown in the two images.

It is possible to direct a light containing a first light and a second light to the substrate as in the first embodiment, and it is also possible to direct a first light and a second light independently to the substrate as in the second embodiment. It is noted that both embodiments are within the scope of the technical concept of the present invention. Another embodiment of directing the light containing the first light and the second light to the substrate is to direct a light having a certain cross section to the surface and to sort the reflected light from the surface into predetermined plural zones which are defined as a first light, a second light, . . . , and so forth. In this case, an angle of incidence of the light is preferably not less than 50 degrees.

Figure 10:
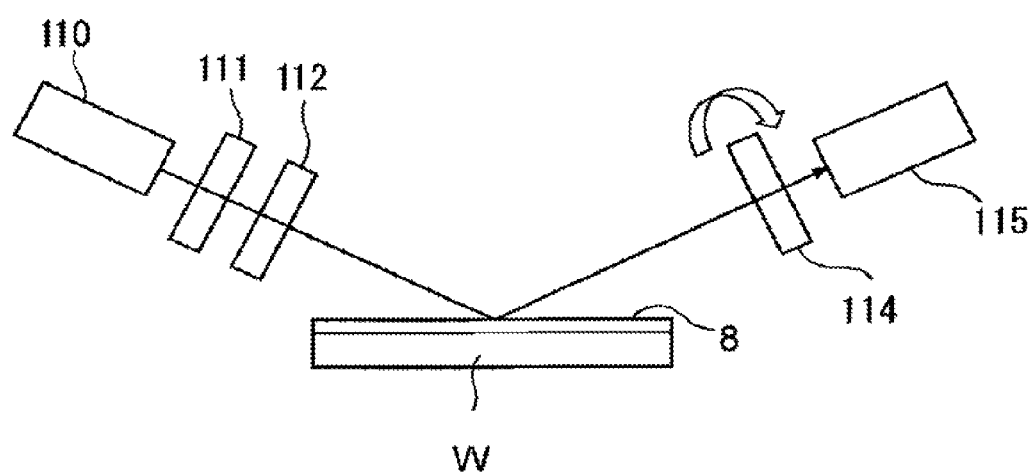
FIG. 10 is a view for illustrating a principle of a polishing end point detection according to another embodiment of the present invention.

FIG. 10 is a view for illustrating a principle of a polishing end point detection method according to another embodiment of the present invention. In this embodiment, an ellipsometer shown in FIG. 10 is used to measure two parameters $\Delta$ and $\psi$ which indicate a phase difference between p-polarized light and s-polarized light and an amplitude ratio of the p-polarized light to the s-polarized light, respectively. The ellipsometer shown in FIG. 10 is a rotary-polarizer-type ellipsometer.

In FIG. 10, a light source 110 emits light, which is converted into linearly-polarized light by passing through a polarizer 111. This linearly-polarized light passes through a phase plate 112 and impinges upon a surface of a film 8 on a substrate W. The polarizer 111 is fixed and is configured to produce linearly-polarized light that is inclined (i.e., polarized) at an angle of, for example, 45 degrees with respect to a plane of incidence (i.e., a plane containing an incident light and a reflected light). The reflected light from the substrate W including the film 8 passes through a polarizer 114 and is received by a photodetector 115. The polarizer 114 is configured to be rotated by a non-illustrated motor. During measuring, the polarizer 114 is rotated by the motor, and the parameters $\Delta$ and $\psi$ are calculated from a rotational angle of the polarizer 114 and an intensity of the reflected light obtained by the photodetector 115. A known technique can be used to calculate the two values $\Delta$ and $\psi$.

The measurements of $\Delta$ and $\psi$ are plotted on a $\psi$-$\Delta$ coordinate system having a vertical axis indicating $\Delta$ and a horizontal axis indicating $\psi$. Coordinates [$\psi$, $\Delta$], which indicate measurements, move to describe a certain track on the $\psi$-$\Delta$ coordinate system as a polishing time elapses (i.e., as a thickness of the film is reduced). This track of the coordinates [$\psi$, $\Delta$] depends on types of medium, film, and substrate and a wavelength of the light. In other words, as long as types of medium, film, and substrate and a wavelength of the light remain unchanged, the coordinates [$\psi$, $\Delta$] describe a track with identical regularity as the thickness of the film decreases.

Figure 11A:
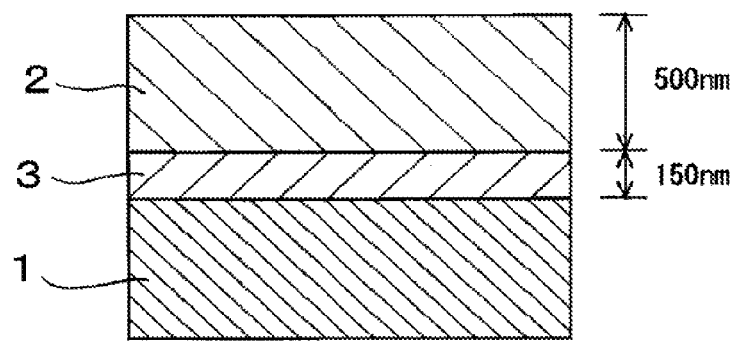
FIGS. 11A through 11C are cross-sectional views each showing a multilayer structure in which a SiN film having a thickness of 150 nm is formed on a Si substrate and a $SiO_2$ film having a thickness of 500 nm is formed on the SiN film.
Figure 11B:
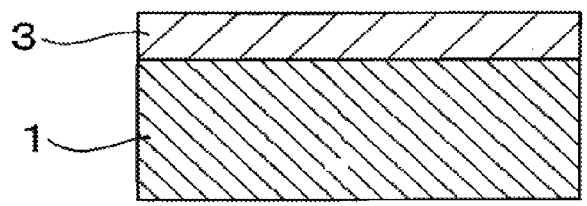
Figure 11C:
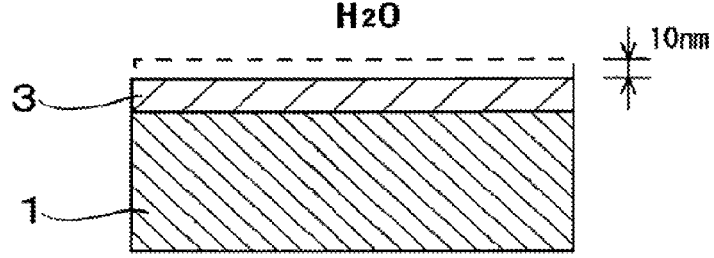

FIG. 11A through FIG. 11C are cross-sectional views each showing a multilayer structure in which a SiN film 3 having a thickness of 150 nm is formed on a Si substrate 1 and a $SiO_2$ film 2 having a thickness of 500 nm is formed on the SiN film 3. Pure water ($H_2O$) is used as the medium contacting the $SiO_2$ film 2 which is an uppermost layer. Air may be used as the medium. In this polishing process, the $SiO_2$ film 2 on the SiN film 3 is removed completely (see FIG. 11B) and polishing is stopped when the SiN film 3 is removed by up to 10 nm (see FIG. 11C). Preferably, polishing is stopped when the $SiO_2$ film 2 is completely removed.

Figure 12:
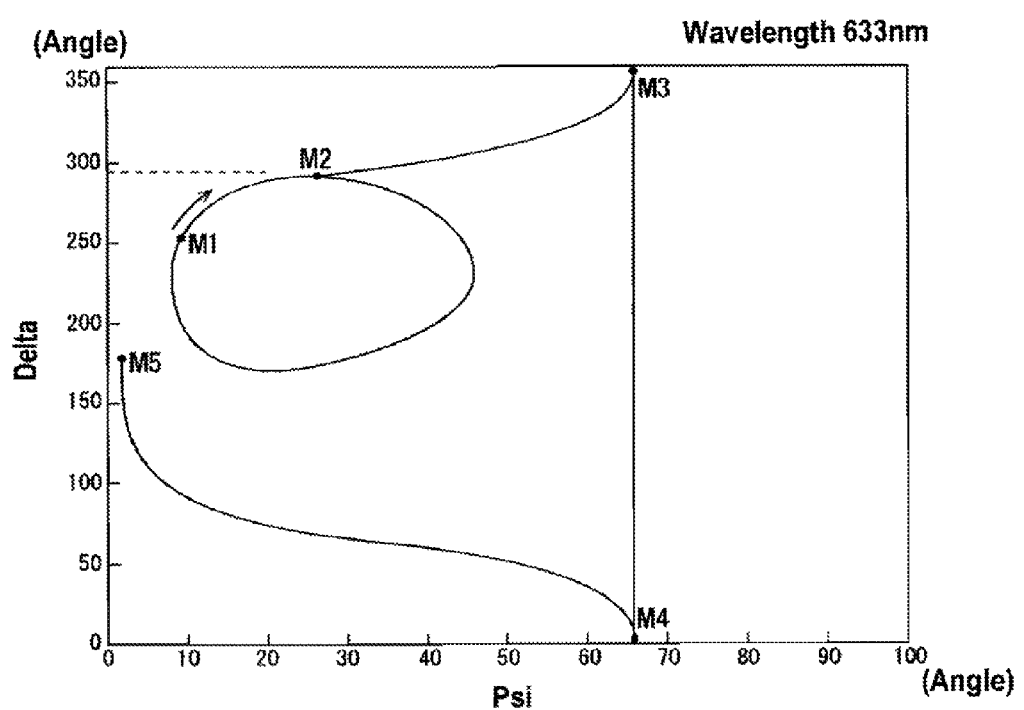
FIG. 12 is a diagram showing a track of coordinates $[\psi, \Delta]$ obtained by plotting values of $\Delta$ and $\psi$, measured during polishing, on a $\psi$-$\Delta$ coordinate system.

FIG. 12 is a diagram showing a track of the coordinates [$\psi$, $\Delta$] described by plotting the values of $\Delta$ and $\psi$, measured during polishing, on the $\psi$-$\Delta$ coordinate system. In FIG. 12, light having a wavelength of 633 nm is used. As shown in FIG. 12, the coordinates [$\psi$, $\Delta$] start from a point M1 and move to describe an elliptical track while the $SiO_2$ film is being polished. When the $SiO_2$ film is removed, the coordinates [$\psi$, $\Delta$] deviate from the elliptical track, and describe a different track.

Deviation of the coordinates [$\psi$, $\Delta$] from the elliptical track means that removal of the $SiO_2$ film and exposure of the underlying SiN film. In FIG. 12, the coordinates at this removal point are indicated by a point M2. While the SiN film is being polished (removed), the coordinates move to describe a certain track that is different from the elliptical track in polishing of the $SiO_2$ film (see a point M3 and a point M4). A point M5 indicates a time point when the SiN film is completely removed. Although it seems to be discontinuous change between the point M3 and the point M4, it is actually a continuous change because the point M3 ($\Delta$=360°) and the point M4 ($\Delta$=0°) are identical to each other.

The time point of removal of the $SiO_2$ film shown in FIG. 11B corresponds to the point M2 in FIG. 12. Therefore, the polishing end point can be detected by monitoring the track of the coordinates [$\psi$, $\Delta$] during polishing and detecting the point (M2) where the coordinates deviate from the regular track (i.e., the regularity of the track). The same result can also be obtained by plotting coordinates [$\Delta$, $\psi$] on a $\Delta$-$\psi$ coordinate system having a vertical axis indicating $\psi$ and a horizontal axis indicating $\Delta$.

There are several ways of detecting the deviation of the coordinate track (i.e., removal of the $SiO_2$ film). One example for detecting the deviation of the coordinate track is to create in advance a range of the track of the coordinates or a threshold and to determine whether the coordinates exceed the preset range or the threshold. In the example shown in FIG. 12, during polishing of the $SiO_2$ film, the coordinates [$\psi$, $\Delta$] move in the elliptical orbit (track). On the other hand, during polishing of the SiN film, the coordinates [$\psi$, $\Delta$] describe a different track that starts from nearly a top (i.e., a highest point) of the elliptical track. Thus, in this example, a value 300° is set in advance as the threshold of $\Delta$ during polishing of the $SiO_2$ film, because the value 300° is close to the top of the elliptical track. The deviation of the coordinate track (i.e., the removal of the $SiO_2$ film) can be determined by detecting that the value of $\Delta$ exceeds the preset threshold 300°.

Figure 13:
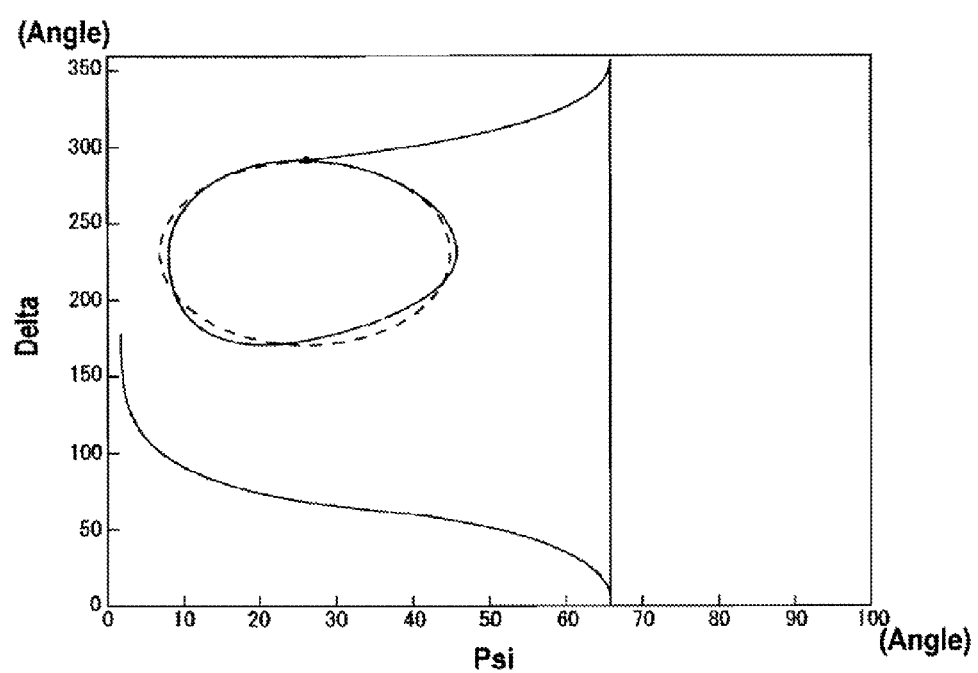
FIG. 13 is a diagram for illustrating an example of detecting the deviation of the coordinate track.

FIG. 13 is a diagram for illustrating another example of detecting the deviation of the coordinate track (i.e., the track of the coordinates). In this example, the coordinate track indicating polishing of the $SiO_2$ film is expressed by an approximate mathematical formula. More specifically, as indicated by a dotted line, the coordinate track, which indicates polishing of the $SiO_2$ film, is roughly expressed by using the following formula of ellipse.

$$(\psi-\alpha)^2/a^2+(\Delta-\beta)^2/b^2=1 \quad (1)$$

From the above formula (1), the next equation (2) is derived.

$$\Delta=\beta\pm(b/a)\times[\{a+(\psi-\alpha)\}\{a-(\psi-\alpha)\}]^{1/2} \quad (2)$$

In this equation (2), constants "a, b, α, β" are given in advance by actual measurements or theoretical values. For example, in the example shown in FIG. 13, the constant "a" is set to be about 20, the constant "b" is set to be about 60, the constant "α" is set to be about 27, and the constant "β" is set to be about 230. The values of Δ and ψ are given by the above-mentioned measuring process. The measurement of ψ is substituted in the equation (2), so that estimated values Δtar1 and Δtar2 are obtained. Then, the measurement of Δ and the estimated values Δtar1 and Δtar2 are compared using the following formulas (3) and (4).

$$\Delta tar1 - C < \text{the measurement of } \Delta < \Delta tar1 + C \quad (3)$$

$$\Delta tar2 - C < \text{the measurement of } \Delta < \Delta tar2 + C \quad (4)$$

In the above formulas (3) and (4), "C" is a permissible value determined depending on a detection capability. In order to quickly detect the removal of the $SiO_2$ film, "C" is preferably not more than 0.5 degree.

If the measurement of Δ does not satisfy both the formulas (3) and (4), the $SiO_2$ film is determined to be removed. If the measurement of Δ satisfies one of the above formulas (3) and (4), the $SiO_2$ film is determined to still remain. For example, substituting 40 degrees as the measurement of ψ into the equation (2), two solutions 184 and 275 (=Δtar1 and Δtar2) are obtained, where the constants "a", "b", "α", and "β" are about 20, 60, 27, and 230, respectively. If the permissible value "C" is 2 degrees, then the ranges of the value of Δ are given from the above formulas (3) and (4) as follows.

$$182 < \text{the measurement of } \Delta < 186 \quad (3)'$$

$$273 < \text{the measurement of } \Delta < 277 \quad (4)'$$

The above-described methods of detecting the deviation of the coordinate track are examples, and the present invention is not limited to these methods. For example, a table, which stores values of ψ and Δ obtained during polishing of the $SiO_2$ film and permissible values (e.g., ranges or thresholds) close to the stored values ψ and Δ, may be prepared in advance. In this case also, it is possible to determine the deviation of the coordinate track upon detecting that the measurements of ψ and Δ are beyond the permissible values defined in the table. In another example, several reference coordinate tracks, each having a regularity varying depending on a type of film, may be prepared in advance. In this case, the polishing end point is detected by determining what reference coordinate track matches the coordinate track obtained during polishing.

Plotting of the coordinates onto the ψ-Δ coordinate system does not necessarily mean that creating an actual ψ-Δ coordinate system and plotting the coordinates [ψ, Δ] onto the created ψ-Δ coordinate system. For example, plotting of the coordinates onto the ψ-Δ coordinate system includes memorizing (or storing) the measurements of ψ and Δ as the coordinates. In this case also, the deviation of the coordinate track can be determined by detecting that the measurements of ψ and Δ exceed the preset ranges or thresholds.

Figure 14:
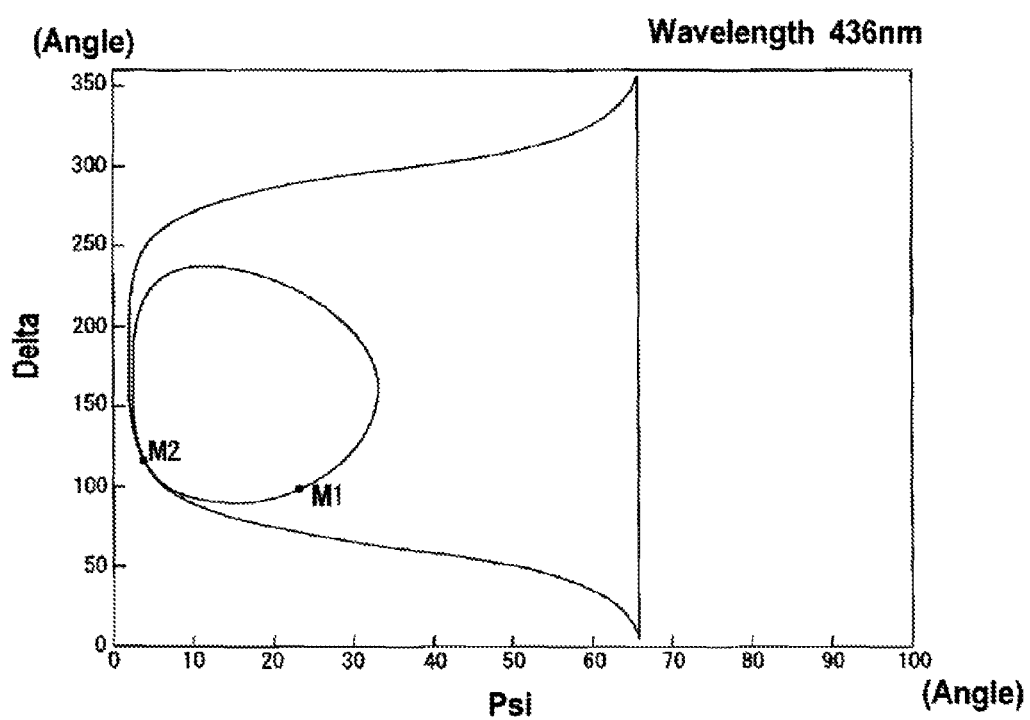
FIG. 14 is a diagram showing a track described by the moving coordinates $[\psi, \Delta]$ on the coordinate system when using a light having a wavelength of 436 nm.

FIG. 14 is a diagram showing a track described by the moving coordinates [ψ, Δ] on the coordinate system when using light having a wavelength of 436 nm. As shown in FIG. 14, a first track of the coordinates during polishing of the $SiO_2$ film changes into a second track of the coordinates during polishing of the SiN film at the point M2. However, these two tracks overlap each other around at the point M2. As a result, it is difficult to detect the point M2 indicating the removal of the $SiO_2$ film. In this manner, the track of the coordinates changes depending on the wavelength of the light. Therefore, it is preferable to select the wavelength of the light such that the changing point (i.e., the polishing end point) M2 appears clearly on the ψ-Δ coordinate system.

Figure 15A:
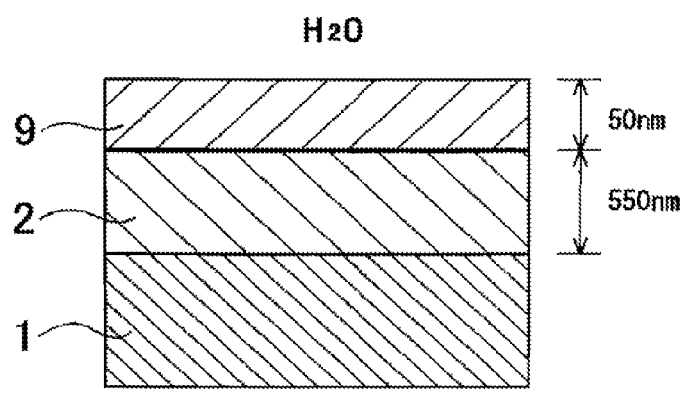
FIG. 15A is a cross-sectional view showing a multilayer structure in which a $SiO_2$ film is formed on a Si substrate and a Cu film is formed on the $SiO_2$ film.
Figure 15B:
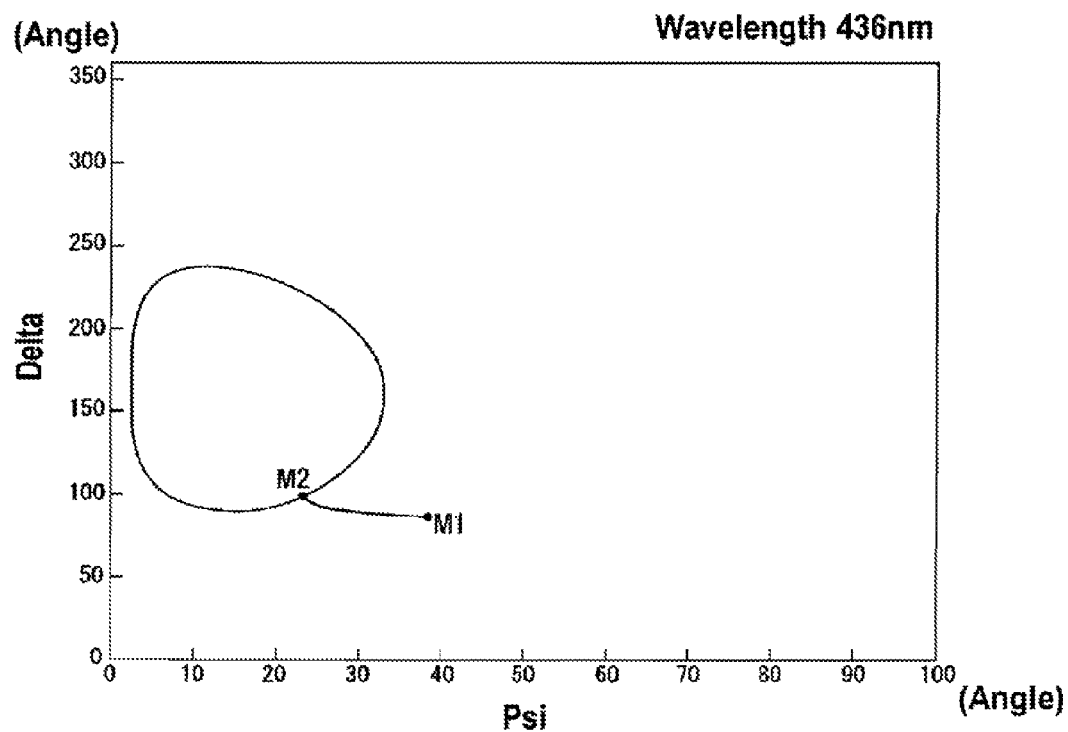
FIG. 15B is a diagram illustrating a track of the coordinates $[\psi, \Delta]$ when polishing the Cu film and the $SiO_2$ film shown in FIG. 15A.

FIG. 15A is a cross-sectional view showing a multilayer structure in which a $SiO_2$ film 2 is formed on a Si substrate 1 and a Cu film 9 is formed on the $SiO_2$ film 2. FIG. 15B is a diagram illustrating a track of the coordinates [ψ, Δ] when polishing the Cu film and the $SiO_2$ film shown in FIG. 15A. Pure water ($H_2O$) is used as the medium, and light having a wavelength of 436 nm is used.

In FIG. 15B, a point M1 indicates a polishing start point of the Cu film. During polishing of the Cu film, the coordinates [ψ, Δ] move substantially horizontally. A point M2 indicates a time point when the Cu film is removed and the underlying $SiO_2$ film is exposed. During polishing of the $SiO_2$ film, the coordinates [ψ, Δ] move to describe a track that is identical to that shown in FIG. 14. As can be seen from the FIG. 15B, the changing point (polishing end point) M2 from polishing of the Cu film into polishing of the $SiO_2$ film appears relatively clearly on the ψ-Δ coordinate system. In this manner, the present invention can be applied not only to the multilayer structure containing the insulating films (e.g., the $SiO_2$ film and the SiN film), but also to the multilayer structure containing the metal film and the insulating film.

Figure 16:
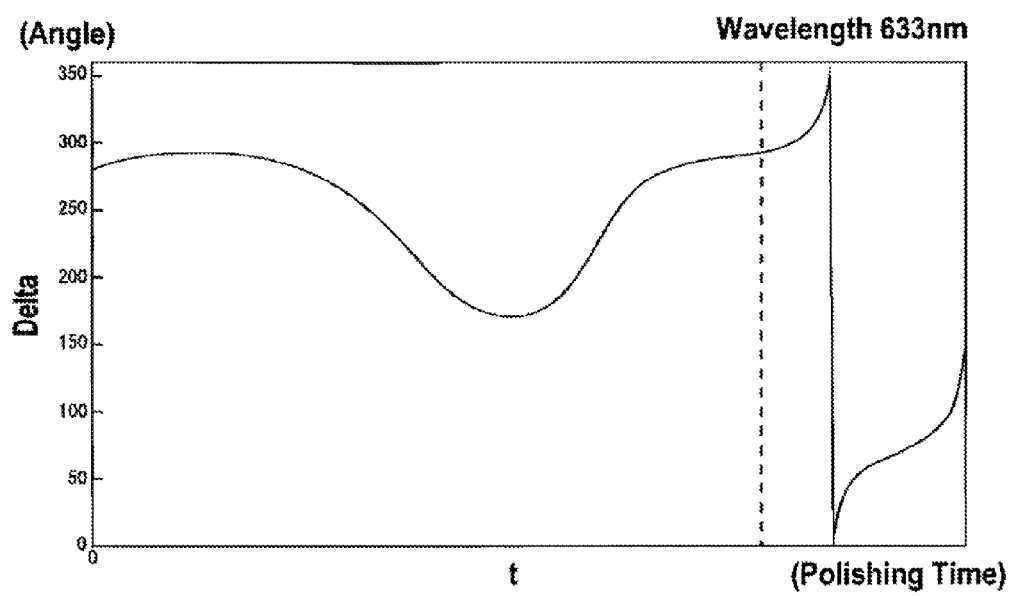
FIG. 16 is a graph showing a change in value of $\Delta$ with time.
Figure 17:
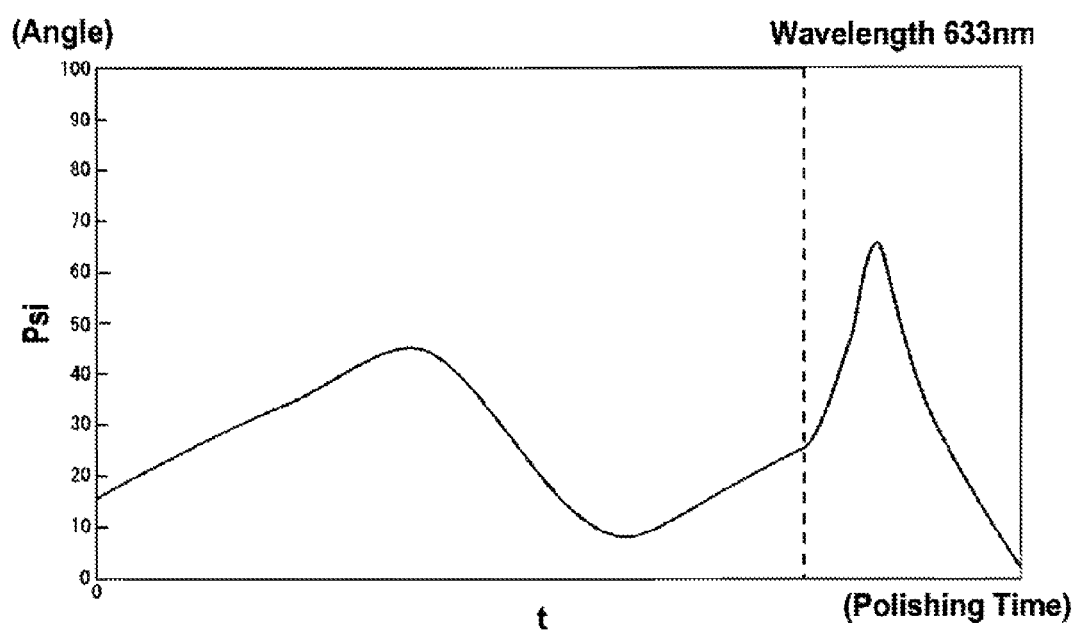
FIG. 17 is a graph showing a change in value of $\psi$ with time.

Next, a polishing end point detection method according to another embodiment of the present invention will be described. This embodiment detects the polishing end point by monitoring a change in value of Δ or ψ with time. FIG. 16 is a graph showing the change in value of Δ with time, and FIG. 17 is a graph showing the change in value of ψ with time. In FIG. 16 and FIG. 17, a dotted line indicates a time point when the $SiO_2$ film is removed and the underlying SiN film is exposed. Although the value of Δ in FIG. 16 seems to change discontinuously at an angle of 360 degrees, this is actually a continuous change because the angle of 360 degrees and the angle of 0 degree in Δ are identical to each other.

When the film on the substrate is being polished under a condition that a polishing rate is constant, each of the values of Δ and ψ changes regularly on substantially a constant cycle that depends on the wavelength of the light. This is due to an optical interference as a result of multiple reflection on the surface of the film and an interface between the film and the substrate. The Δ and ψ are values each indicating a polarization state, and these values change in accordance with an interaction between the incident light and the film on the substrate. Therefore, the manner of changes in values of Δ and ψ changes depending on a type of film exposed.

In FIG. 16, coordinates [t, Δ] are plotted on a t-Δ coordinate system having a vertical axis indicating Δ and a horizontal axis indicating a polishing time (t). In FIG. 17, coordinates [t, ψ] are plotted on a t-Δ coordinate system having a vertical axis indicating ψ and a horizontal axis indicating the polishing time (t). As shown in FIG. 16 and FIG. 17, a track of the coordinates when polishing the $SiO_2$ film and a track of the coordinates when polishing the SiN film are different from each other. Therefore, detection of the polishing end point (i.e., the removal of the $SiO_2$ film) can be performed by detecting the deviation of the coordinates from the regularity of the track of the coordinates. Like the above-described embodiment, a method of detecting a time point when the values of Δ and ψ exceed preset ranges or thresholds can be used as a specific method of detecting a changing point of the track of the coordinates.

Figure 18:
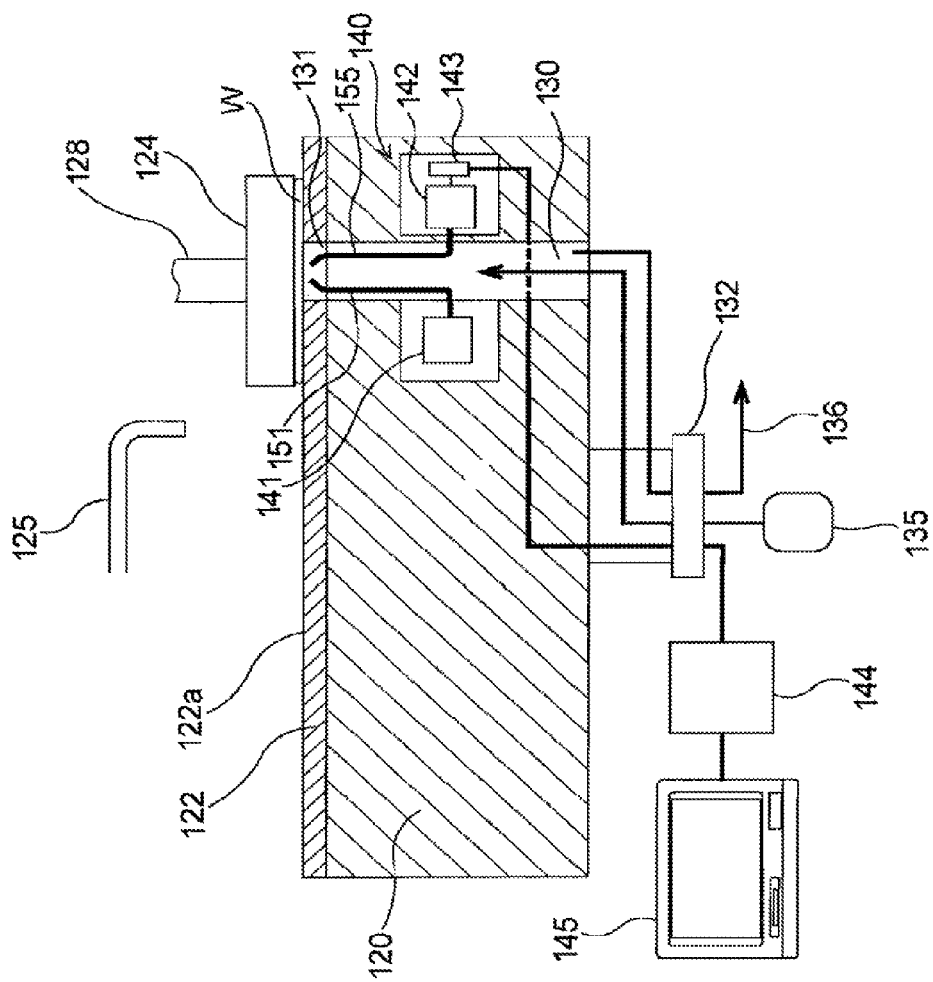
FIG. 18 is a schematic view showing a polishing apparatus according to an embodiment of the present invention.

FIG. 18 is a schematic view showing a polishing apparatus according to an embodiment of the present invention. As shown in FIG. 18, the polishing apparatus includes a polishing table 120 supporting a polishing pad 122, a top ring (pressing mechanism) 124 configured to hold a substrate W (i.e., a workpiece to be polished) and to press the substrate W against the polishing pad 122, and a polishing liquid supply nozzle 125 configured to supply a polishing liquid (slurry) onto the polishing pad 122. The polishing table 120 is coupled to a motor (not shown in the drawing) provided below the polishing table 120, so that the polishing table 120 is rotated about its own axis. The polishing pad 122 is attached to an upper surface of the polishing table 120.

The polishing pad 122 has an upper surface 122a, which provides a polishing surface where the substrate W is polished as a result of sliding contact with the polishing surface. The top ring 124 is coupled to a motor and an elevating cylinder (not shown in the drawing) via a top ring shaft 128. This configuration allows the top ring 124 to move vertically and to rotate about the top ring shaft 128. The top ring 124 has a lower surface which is configured to hold the substrate W by a vacuum suction or the like.

The substrate W, held on the lower surface of the top ring 124, is rotated by the top ring 124, and is pressed against the polishing pad 122 on the rotating polishing table 120. During the sliding contact between the substrate W and the polishing pad 122, the polishing liquid is supplied onto the polishing surface 122a of the polishing pad 122 from the polishing liquid supply nozzle 125. In this manner, the substrate W is polished with the polishing liquid being present between the substrate W and the polishing pad 122. In this embodiment, a mechanism of providing relative motion between the substrate W and the polishing pad 122 is constructed by the polishing table 120 and the top ring 124.

The polishing table 120 has a hole 130 which has an upper end lying in the upper surface of the polishing table 120. The polishing pad 122 has a through-hole 131 at a position corresponding to the hole 130. The hole 130 and the through-hole 131 are in fluid communication with each other. The through-hole 131 has an upper end lying in the polishing surface 122a. A diameter of the through-hole 131 is about 3 mm. The hole 130 is coupled to a liquid supply source 135 and a discharge passage 136 via a rotary joint 132. The liquid supply source 135 is configured to supply water (preferably pure water) as a transparent liquid into the hole 130 during polishing. The pure water fills a space formed by a lower surface of the substrate W and the through-hole 131, and is then expelled therefrom through the discharge passage 136.

The polishing apparatus has a polishing end point detection unit 140 for detecting a polishing end point of the substrate W. This polishing end point detection unit 140 includes a light emitter 141 configured to emit a light (preferably a white light) to the substrate W, a light receiver 142 configured to receive the light reflected from the substrate W, and a calculating section 143 configured to obtain the amplitude ratio ψ and the phase difference Δ. The light emitter 141 and the light receiver 142 are disposed in the polishing table 120. The polishing end point detection unit 140 further includes a determining section 144 configured to detect the polishing end point from the amplitude ratio ψ and the phase difference Δ obtained by the calculating section 143.

Figure 19A:
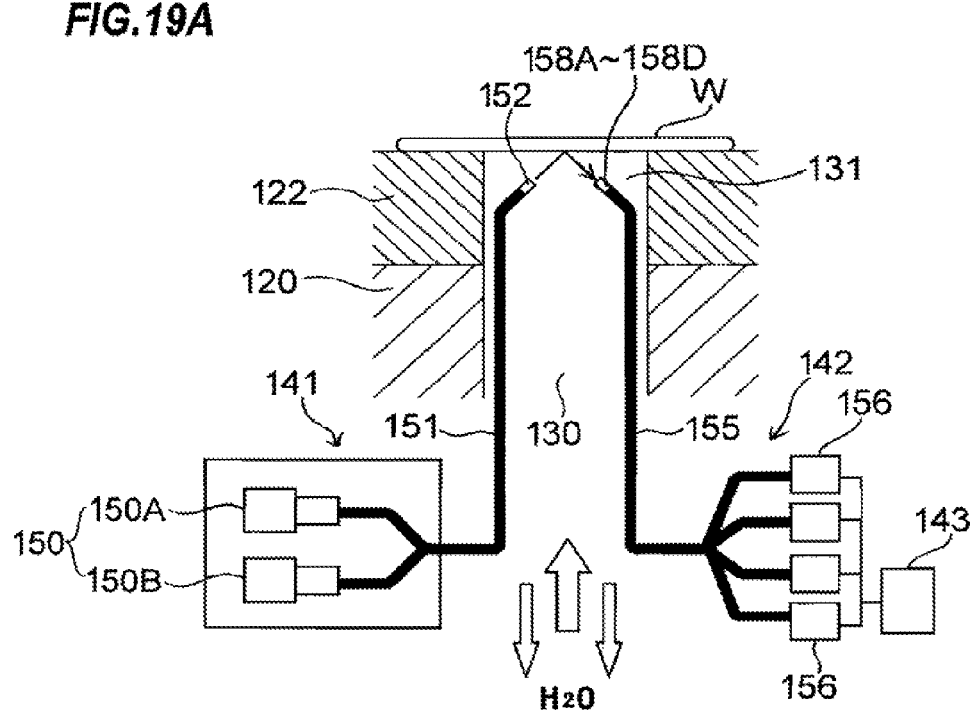
FIG. 19A is an enlarged view showing a light emitter and a light receiver of a polishing end point detection unit shown in FIG. 18.

FIG. 19A is an enlarged view showing the light emitter 141 and the light receiver 142 of the polishing end point detection unit 140. As shown in FIG. 19A, the light emitter 141 includes a light source 150 having a first light source 150A and a second light source 150B, an optical fiber 151 configured to direct the light from the light source 150 to the film on the substrate W, and a polarizer 152 mounted on an outlet of the optical fiber 151. The optical fiber 151 extends from the light source 150 to a position near the surface W through the hole 130 and the through-hole 131.

Figure 19B:
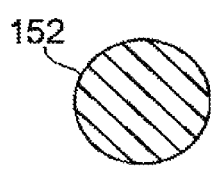
FIG. 19B is a plan view showing a polarizer.

FIG. 19B is a plan view showing the polarizer. The polarizer 152 is attached to the optical fiber 151 such that the polarizer 152 is inclined at an angle of 45 degrees with respect to a plane of incidence, as shown in FIG. 19B. The light from the light source 150 is guided by the optical fiber 151 to pass through the polarizer 152. The light is converted into linearly-polarized light inclined at an angle of 45 degrees with respect to the plane of incidence by passing through the polarizer 152. This linearly-polarized light is incident obliquely on a surface of the film on the substrate W. An angle of incidence of the light is preferably in a range of Brewster's angle ±10 degrees. This Brewster's angle is determined from an index of infraction of the film (i.e., an uppermost film of the multilayer film) and an index of infraction of a medium (the water in this embodiment).

The first light source 150A is configured to emit a light having a first wavelength and the second light source 150B is configured to emit a light having a second wavelength which is different from the first wavelength. Therefore, by switching between the first light source 150A and the second light source 150B, the wavelength of the light to be incident on the film can be changed. A light emitting diode (LED), a pulsed light emitter, or a white light emitter can be used as the first light source 150A and the second light source 150B. It is possible to provide three or more light sources each configured to emit a light having a wavelength differing from another.

The light receiver 142 includes four optical fibers 155 configured to receive the reflected light from the substrate W including the film, and photodetectors 156 connected to the optical fibers 155, respectively. In FIG. 19A, the four optical fibers 155 are bundled together. Four polarizers 158A, 158B, 158C, and 158D are mounted on tip ends of the optical fibers 155, respectively. The reflected light from the substrate W passes through the four polarizers 158A, 158B, 158C, and 158D, and is guided by the four optical fibers 155 and received by the four photodetectors 156. Each of the photodetectors 156 is configured to measure an intensity of the light that has passed through each polarizer. A photodiode or an image sensor (e.g., CCD) can be used as the photodetector 156. When the white light emitter is used as the light source, a spectral filter is disposed between the optical fibers 155 and the photodetectors 156.

Figure 19C:
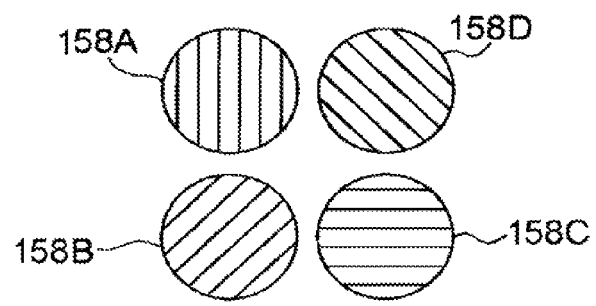
FIG. 19C is a plan view showing an arrangement of four polarizers.

FIG. 19C is a plan view showing an arrangement of the four polarizers 158A, 158B, 158C, and 158D. As shown in FIG. 19C, the four polarizers 158A, 158B, 158C, and 158D are arranged at different angles. More specifically, the polarizer 158A is arranged at an angle of 0 degree from the plane of incidence, the polarizer 158B is arranged at an angle of 45 degrees from the plane of incidence, the polarizer 158C is arranged at an angle of 90 degrees from the plane of incidence, and the polarizer 158D is arranged at an angle of 135 degrees from the plane of incidence.

The photodetectors 156 are coupled to the calculating section 143. This calculating section 143 is configured to calculate a phase difference Δ between p-polarized light and s-polarized light and an amplitude ratio ψ of the p-polarized light to the s-polarized light from intensities of the reflected light that has passed through the four polarizers 158A, 158B, 158C, and 158D. An example of algorithm of calculating the phase difference and the amplitude ratio will be described below.

Figure 20:
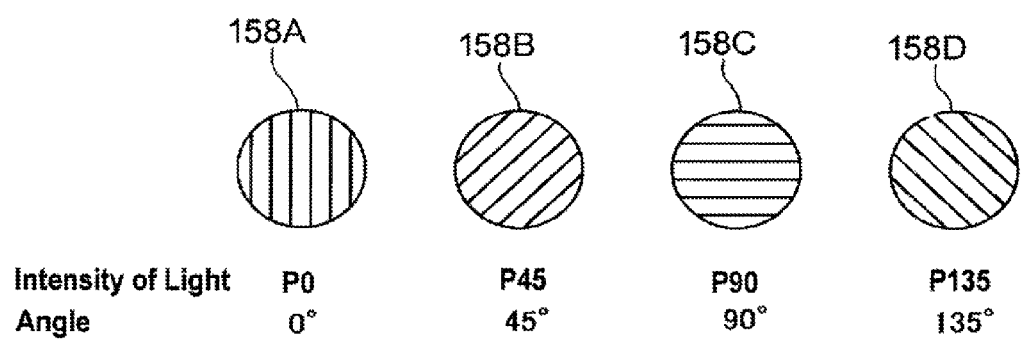
FIG. 20 is a view illustrating four values indicating intensities of the light that has passed through the four polarizers.

As described above, the intensities (mW) of the light, that has passed through the polarizers 158A, 158B, 158C, and 158D, are measured by the photodetectors 156, respectively. Hereinafter, four values indicating the intensities of the light, that has passed through the polarizers 158A, 158B, 158C, and 158D, will be referred to as P0, P45, P90, and P135 for convenience's sake, as shown in FIG. 20. The calculating section 143 selects highest two intensities (i.e., a highest intensity and a second-highest intensity) from the P0, P45, P90, and P135. The selected intensities of the light will be defined to as [W1, W2] in this specification.

The selected pair of intensities [W1, W2] is any one of the following four combinations: [P0, P45], [P45, P90], [P90, P135], and [P135, P0]. If the other combinations are selected or if a difference between the selected intensities and the non-selected intensities is small, the calculating section 143 determines that the calculation of the phase difference $\Delta$ and the amplitude ratio $\psi$ cannot be performed for the reasons that the non-polarized light or the polarized light is weak.

From the selected two intensities of the light, the phase difference $\Delta$ is calculated using the following equation (5).

$$\Delta = W2 \times 45/(W1+W2) + \text{reference angle} \quad (5)$$

In this equation, the reference angle is the angle of the polarizer selected for W1.

For example, when the combination [P45(=1 mW), P90(=3 mW)] is selected as [W1, W2], the reference angle is 45 degrees. The value of $\Delta$ is given by the above equation (5) as follows.

$$\Delta = 3 \times 45/(1+3) + 45 = 78.75 \text{ degrees.}$$

This method of obtaining the phase difference $\Delta$ is a method of obtaining a peak of a polarizing direction using a linear interpolation formula. However, the interpolation formula is not limited to the linear interpolation formula.

On the other hand, since the amplitude ratio $\psi$ is a ratio of the intensity of the p-polarized light to the intensity of the s-polarized light, the amplitude ratio $\psi$ is given by the following equation.

$$\psi = (P0)/(P90) \quad (6)$$

In this manner, by using the four polarizers 158A, 158B, 158C, and 158D arranged at different angles, the phase difference $\Delta$ and the amplitude ratio $\psi$ can be obtained without rotating the polarizer itself.

In the above-described polishing apparatus, instead of the four polarizers, it is possible to employ a conventional rotary-polarizer-type structure configured to measure the phase difference $\Delta$ and the amplitude ratio $\psi$ while rotating a single polarizer. However, according to the above-described embodiment, because the polarizers are not required to rotate, the phase difference $\Delta$ and the amplitude ratio $\psi$ can be obtained in a short period of time, as compared with the conventional rotary-polarizer-type structure.

During polishing, the water (preferably pure water) is flowing through the hole 130 and the through-hole 131. Therefore, the polishing liquid is expelled together with the water, and as a result the path of light can be secured. Using the phase difference $\Delta$ and the amplitude ratio $\psi$ obtained by the calculating section 143, the determining section 144 detects the polishing end point according to the above-described polishing end point detection method. The determining section 144 sends a signal indicating the detection of the polishing end point to the controller 145. Upon receiving this signal, the controller 145 stops the polishing operation of the polishing apparatus. In order to improve the reliability of the polishing end point detection, it is preferable that the controller 145 stop the polishing operation after a predetermined time has elapsed since the controller 145 has received the signal from the determining section 144.

Figure 21:
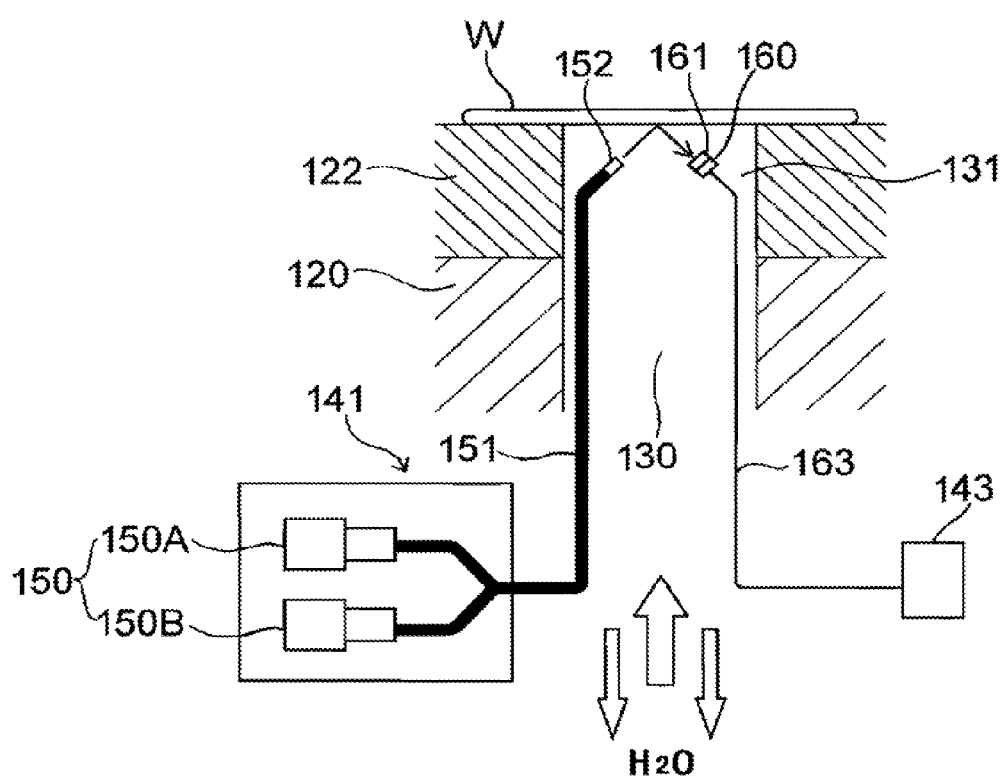
FIG. 21 is an enlarged view showing another example of the polishing end point detection unit.

FIG. 21 is an enlarged view showing another structural example of the polishing end point detection unit. In this example, a CCD (image sensor) 160 is used as the photodetector (light-receiving device). This CCD 160 is located in the through-hole 131 formed in the polishing table 122. A polarizer array 161 having plural polarizers is attached to a front surface of the CCD 160.

Figure 22A:
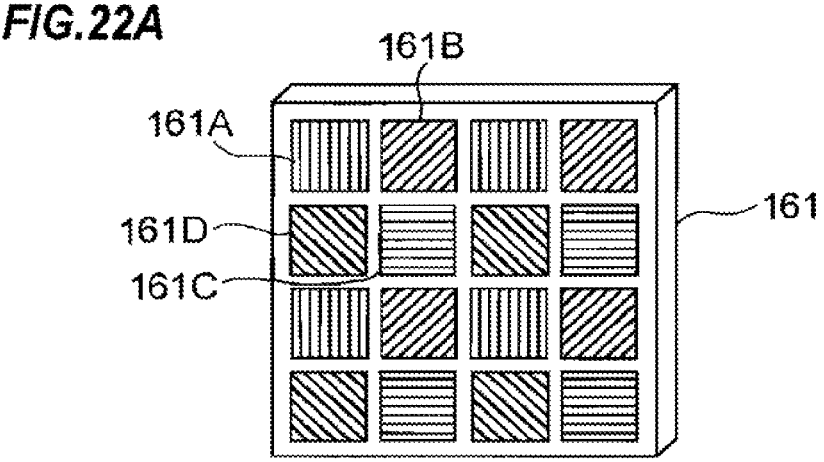
FIG. 22A is a schematic view showing a polarizer array.

FIG. 22A is a schematic view showing the polarizer array. As shown in FIG. 22A, the polarizer array 161 has the plural polarizers arranged regularly. These polarizers comprise four types of polarizers 161A, 161B, 161C, and 161D arranged at different angles, like the polarizers 158A, 158B, 158C, and 158D shown in FIG. 19C. More specifically, the polarizer 161A is arranged at an angle of 0 degree from the plane of incidence, the polarizer 161B is arranged at an angle of 45 degrees from the plane of incidence, the polarizer 161C is arranged at an angle of 90 degrees from the plane of incidence, and the polarizer 161D is arranged at an angle of 135 degrees from the plane of incidence.

Figure 22B:
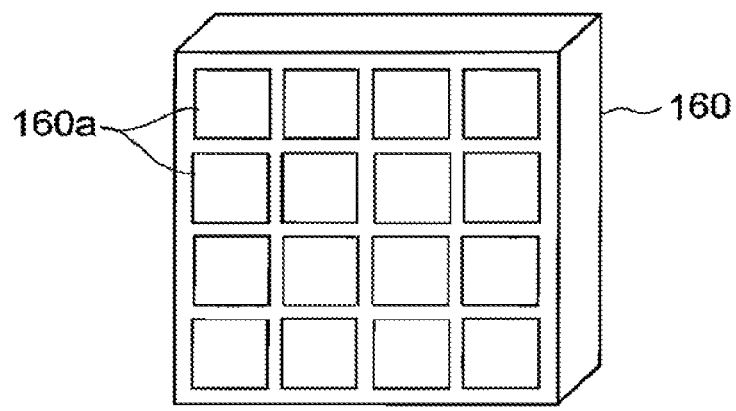
FIG. 22B is a schematic view showing a CCD.
Figure 22C:
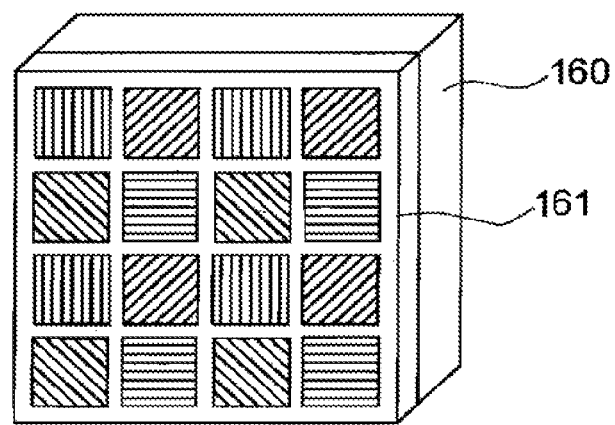
FIG. 22C is a view showing a combination of the polarizer array shown in FIG. 22A and the CCD shown in FIG. 22B.

FIG. 22B is a schematic view showing the CCD, and FIG. 22C is a view showing a combination of the polarizer array shown in FIG. 22A and the CCD shown in FIG. 22B. The polarizer array 161 is, as shown in FIG. 22C, provided on the front surface of the CCD 160. Each polarizer of the polarizer array 161 is attached to a front surface of each pixel 160a of the CCD 160. Therefore, each pixel 160a receives the light that has passed through one of the four polarizers 161A, 161B, 161C, and 161D. The CCD 160 is coupled to the calculating section 143 via a cable 163. The calculating section 143 calculates the phase difference $\Delta$ and the amplitude ratio $\psi$ using the same algorithm as described in the previous example using the four polarizers.

The previous description of embodiments is provided to enable a person skilled in the art to make and use the present invention. Moreover, various modifications to these embodiments will be readily apparent to those skilled in the art, and the generic principles and specific examples defined herein may be applied to other embodiments. Therefore, the present invention is not intended to be limited to the embodiments described herein but is to be accorded the widest scope as defined by limitation of the claims and equivalents.

What is claimed is:

1. A method of detecting a polishing end point of a workpiece having an upper layer and an underlying lower layer, said method comprising:
  emitting a first light and a second light to a surface of the workpiece at a first angle of incidence and a second angle of incidence, respectively;
  receiving the first light and the second light reflected from the surface through a polarizing filter;
  performing a first analyzing process of analyzing a brightness and a saturation of the surface from the first light received;
  performing a second analyzing process of analyzing a brightness and a saturation of the surface from the second light received; and
  determining removal of the upper layer based on changes in the brightness and the saturation of the surface.

2. The method according to claim 1, wherein:
  the first angle of incidence is an angle selected from a range of a first Brewster's angle ±10 degrees, the first Brewster's angle depending on the upper layer; and
  the second angle of incidence is an angle selected from a range of a second Brewster's angle ±10 degrees, the second Brewster's angle depending on the lower layer.

3. The method according to claim 1, wherein said determining of removal of the upper layer comprises determining removal of the upper layer by detecting an abrupt changes in the brightness and the saturation of the surface analyzed from at least one of the first light and the second light.

4. The method according to claim 1, wherein said determining of removal of the upper layer comprises determining removal of the upper layer by detecting that the brightness and the saturation of the surface analyzed from the first light exceed the brightness and the saturation of the surface analyzed from the second light.

5. The method according to claim 1, wherein each of said first analyzing process and said second analyzing process includes:
   decomposing a color of the surface into a R component, a G component, and a B component; and
   quantifying the brightness and the saturation of the surface from the R component, the G component, and the B component.

6. The method according to claim 5, wherein each of said first analyzing process and said second analyzing process further includes:
   obtaining a R value, a G value, and a B value representing the quantified R component, the G component, and the B component, respectively;
   calculating a RGB assessment value which is an average, a root mean square, variance, or standard deviation of the R value, the G value, and the B value, or a value given by multiplying the R value, the G value, and the B value by predetermined coefficients, respectively, and summing the resultant values; and
   defining the RGB assessment value as the brightness of the surface.

7. The method according to claim 6, wherein each of said first analyzing process and said second analyzing process further includes:
   calculating a difference between the R value, the G value, and the B value; and
   defining the difference as the saturation of the surface.

8. An apparatus for detecting a polishing end point of a workpiece having an upper layer and an underlying lower layer, said apparatus comprising:
   a light emitter configured to emit a first light and a second light to a surface of the workpiece at a first angle of incidence and a second angle of incidence, respectively;
   a light receiver configured to receive the first light and the second light reflected from the surface;
   a polarizing filter located between the surface of the workpiece and said light receiver; and
   a processing section configured to perform a first analyzing process of analyzing a brightness and a saturation of the surface from the first light received by said light receiver and to perform a second analyzing process of analyzing a brightness and a saturation of the surface from the second light received by said light receiver,
   said processing section being configured to determine removal of the upper layer based on changes in the brightness and the saturation of the surface.

9. The apparatus according to claim 8, wherein:
   the first angle of incidence is an angle selected from a range of a first Brewster's angle ±10 degrees, the first Brewster's angle depending on the upper layer; and
   the second angle of incidence is an angle selected from a range of a second Brewster's angle ±10 degrees, the second Brewster's angle depending on the lower layer.

10. The apparatus according to claim 8, wherein said processing section determines removal of the upper layer by detecting abrupt changes in the brightness and the saturation of the surface analyzed from at least one of the first light and the second light.

11. The apparatus according to claim 8, wherein said processing section determines removal of the upper layer by detecting that the brightness and the saturation of the surface analyzed from the first light exceed the brightness and the saturation of the surface analyzed from the second light.

12. The apparatus according to claim 8, wherein said processing section is configured:
   to decompose a color of the surface into a R component, a G component, and a B component; and
   to quantify the brightness and the saturation of the surface from the R component, the G component, and the B component.

13. The apparatus according to claim 12, wherein said processing section is configured:
   to obtain a R value, a G value, and a B value representing the quantified R component, the G component, and the B component, respectively;
   to calculate a RGB assessment value which is an average, a root mean square, variance, or standard deviation of the R value, the G value, and the B value, or a value given by multiplying the R value, the G value, and the B value by predetermined coefficients, respectively, and summing the resultant values; and
   to define the RGB assessment value as the brightness of the surface.

14. The apparatus according to claim 13, wherein said processing section is configured:
   to calculate a difference between the R value, the G value, and the B value; and
   to define the difference as the saturation of the surface.

15. The apparatus according to claim 8, wherein:
   said light emitter includes a light source, a first lens configured to convert a light from said light source into a parallel light containing the first light and the second light, and a second lens configured to focus the parallel light on a point on the surface of the workpiece; and
   said light receiver is configured to receive the reflected light that has been converted into a parallel light by passing through said second lens.

16. The apparatus according to claim 8, wherein:
   said light emitter includes a light source and two light-emitting optical fibers configured to direct the first light and the second light, respectively, to the surface of the workpiece; and
   said light receiver includes two light-receiving optical fibers arranged at angles corresponding to angles of reflection of the first light and the second light, and two light-receiving devices coupled to said two light-receiving optical fibers, respectively.

17. An apparatus for polishing a workpiece having an upper layer and an underlying lower layer, said apparatus comprising:
   a polishing table configured to support a polishing pad having the polishing surface and a through-hole;
   a top ring configured to press the workpiece against the polishing surface of the polishing pad; and
   a polishing end point detection unit,
   said polishing end point detection unit including
     (i) a light emitter configured to emit a first light and a second light through the through-hole to a surface of the workpiece at a first angle of incidence and a second angle of incidence, respectively,
     (ii) a light receiver configured to receive the first light and the second light reflected from the surface,
     (iii) a polarizing filter located between the surface of the workpiece and said light receiver, and (iv) a processing section configured to perform a first analyzing process of analyzing a brightness and a saturation of the surface from the first light received and to perform a second analyzing process of analyzing a brightness and a saturation of the surface from the second light received, wherein said processing section is configured to determine removal of the upper layer based on changes in the brightness and the saturation of the surface.

18. The apparatus according to claim 17, wherein:
the first angle of incidence is an angle selected from a range of a first Brewster's angle ±10 degrees, the first Brewster's angle depending on the upper layer; and
the second angle of incidence is an angle selected from a range of a second Brewster's angle ±10 degrees, the second Brewster's angle depending on the lower layer.

19. The apparatus according to claim 17, wherein said processing section determines removal of the upper layer by detecting abrupt changes in the brightness and the saturation of the surface analyzed from at least one of the first light and the second light.

20. The apparatus according to claim 17, wherein said processing section determines removal of the upper layer by detecting that the brightness and the saturation of the surface analyzed from the first light exceed the brightness and the saturation of the surface analyzed from the second light.

21. The apparatus according to claim 17, wherein said processing section is configured:
to decompose a color of the surface into a R component, a G component, and a B component; and
to quantify the brightness and the saturation of the surface from the R component, the G component, and the B component.

22. The apparatus according to claim 21, wherein said processing section is configured:
to obtain a R value, a G value, and a B value representing the quantified R component, the G component, and the B component, respectively;
to calculate a RGB assessment value which is an average, a root mean square, variance, or standard deviation of the R value, the G value, and the B value, or a value given by multiplying the R value, the G value, and the B value by predetermined coefficients, respectively, and summing the resultant values; and
to define the RGB assessment value as the brightness of the surface.

23. The apparatus according to claim 22, wherein said processing section is configured:
to calculate a difference between the R value, the G value, and the B value; and
to define the difference as the saturation of the surface.

24. The apparatus according to claim 17, wherein:
said light emitter includes a light source, a first lens configured to convert a light from said light source into a parallel light containing the first light and the second light, and a second lens configured to focus the parallel light on a point on the surface of the workpiece; and
said light receiver is configured to receive the reflected light that has been converted into a parallel light by passing through said second lens.

25. The apparatus according to claim 17, wherein:
said light emitter includes a light source and two light-emitting optical fibers configured to direct the first light and the second light, respectively, to the surface of the workpiece; and
said light receiver includes two light-receiving optical fibers arranged at angles corresponding to angles of reflection of the first light and the second light, and two light-receiving devices coupled to said two light-receiving optical fibers, respectively.

26. The apparatus according to claim 17, further comprising:
a liquid supply source configured to supply a liquid into a space defined by the through-hole and the surface of the workpiece.

* * * * *